US010722775B2

(12) United States Patent
Black et al.

(10) Patent No.: US 10,722,775 B2
(45) Date of Patent: Jul. 28, 2020

(54) ROBOTIC TRAINING SYSTEMS AND METHODS

(71) Applicant: adidas AG, Herzogenaurach (DE)

(72) Inventors: Stephen John Black, Portland, OR (US); Christian Dibenedetto, North Plains, OR (US)

(73) Assignee: adidas AG, Herzogenaurach (DE)

( * ) Notice: Subject to any disclaimer, the term of this patent is extended or adjusted under 35 U.S.C. 154(b) by 557 days.

(21) Appl. No.: 15/277,657

(22) Filed: Sep. 27, 2016

(65) Prior Publication Data

US 2018/0085654 A1    Mar. 29, 2018

(51) Int. Cl.
*A63B 71/06* (2006.01)
*A63B 24/00* (2006.01)
(Continued)

(52) U.S. Cl.
CPC ...... *A63B 71/0686* (2013.01); *A63B 21/0004* (2013.01); *A63B 24/0075* (2013.01);
(Continued)

(58) Field of Classification Search
CPC ........ A63B 24/0062; A63B 2071/0625; A63B 21/0004; A63B 2220/806; A63B 24/0075;
(Continued)

(56) References Cited

U.S. PATENT DOCUMENTS 4,031,510 A * 6/1977 King ...................... G01P 3/489
                                                                 340/670
5,083,968 A * 1/1992 Hart ........................ G09F 27/00
                                                                 446/14
(Continued)

FOREIGN PATENT DOCUMENTS

WO    WO 2011/089506 A1    7/2011
WO    WO 2014/151880 A1    9/2014

OTHER PUBLICATIONS

Engin, M. and Engin, D., "Path Planning of Line Follower Robot," *Proceedings of the 5th European DSP Education and Research Conference*, pp. 1-5, Sep. 13, 2012.

(Continued)

*Primary Examiner* — Eddy Saint-Vil
(74) *Attorney, Agent, or Firm* — Sterne, Kessler, Goldstein & Fox P.L.L.C.

(57) ABSTRACT

A robotic athletic training system may include a mobile robotic platform, a sensor module associated with the mobile robotic platform and configured to obtain data from an environment. The system may include a drive system that propels the platform, as well as a steering system that steers the platform. The system may include a processor which receives data from the sensor module and control the drive system or steering system to follow a path based on the data received from the sensor module. A method may include controlling a robotic athletic training system (or robotic training platform) so that it moves at a velocity. The robotic athletic training system may include a vision system configured to receive data related to a surface and compare a baseline data of a desired surface to the received data and adjusting a travel direction of the robotic system in response to the comparison.

22 Claims, 11 Drawing Sheets

(51) Int. Cl.
    *A63B 21/00* (2006.01)
    *A63B 69/00* (2006.01)
(52) U.S. Cl.
    CPC ...... *A63B 24/0087* (2013.01); *A63B 69/0028* (2013.01); *A63B 71/0622* (2013.01); *A63B 2071/0625* (2013.01); *A63B 2220/806* (2013.01)
(58) Field of Classification Search
    CPC ............ A63B 24/0087; A63B 69/0028; A63B 71/0622; A63B 71/0686
    See application file for complete search history.

(56) References Cited

U.S. PATENT DOCUMENTS

| | | | | |
|---|---|---|---|---|
| 5,213,555 | A * | 5/1993 | Hood | A63B 71/0622 482/57 |
| 5,568,935 | A * | 10/1996 | Mason | B62K 3/005 280/266 |
| 5,645,279 | A * | 7/1997 | Reutlinger | A63F 3/00082 273/249 |
| 5,716,063 | A * | 2/1998 | Doyle | A61H 3/04 135/67 |
| 5,938,564 | A * | 8/1999 | Bachman | A63K 1/02 472/85 |
| 6,152,856 | A * | 11/2000 | Studor | A63B 24/00 434/247 |
| 6,155,582 | A * | 12/2000 | Bourbeau | B62K 13/02 280/204 |
| 6,447,424 | B1 * | 9/2002 | Ashby | A63B 21/005 482/54 |
| 6,468,086 | B1 * | 10/2002 | Brady-Koontz | G09B 5/02 434/257 |
| 6,733,383 | B2 * | 5/2004 | Busse | A63F 13/10 463/6 |
| 6,921,351 | B1 * | 7/2005 | Hickman | G06F 19/3481 482/4 |
| 6,968,592 | B2 * | 11/2005 | Takeuchi | A47L 9/009 15/319 |
| 7,001,313 | B1 * | 2/2006 | Crnkovich | A61H 3/04 135/67 |
| 7,128,693 | B2 * | 10/2006 | Brown | A63B 24/0084 482/8 |
| 7,481,445 | B1 * | 1/2009 | Danziger | A61G 5/08 280/250.1 |
| 7,618,353 | B2 * | 11/2009 | Papadopoulos | A63B 22/02 482/54 |
| 7,625,314 | B2 * | 12/2009 | Ungari | A63B 69/0053 482/1 |
| 7,658,694 | B2 * | 2/2010 | Ungari | A63B 69/0053 482/1 |
| 7,695,406 | B2 * | 4/2010 | Waters | A63B 24/0006 482/8 |
| 7,720,572 | B2 * | 5/2010 | Ziegler | B25J 5/007 700/245 |
| 7,963,885 | B2 * | 6/2011 | Mazzanobile | A63B 69/0053 482/148 |
| 8,346,391 | B1 | 1/2013 | Anhalt et al. | |
| 8,596,658 | B1 * | 12/2013 | Dashew | A61H 3/04 280/87.021 |
| 8,622,874 | B2 * | 1/2014 | Mazzanobile | A63B 69/0053 482/1 |
| 8,682,485 | B2 | 3/2014 | Anhalt et al. | |
| 8,702,566 | B2 * | 4/2014 | Mazzanobile | A63B 69/0028 482/1 |
| 8,892,219 | B2 * | 11/2014 | Pryor | B60K 35/00 382/107 |
| 8,934,995 | B2 * | 1/2015 | Eisner | G06F 15/17306 700/91 |
| 9,039,547 | B2 * | 5/2015 | Yeager | A63B 47/002 473/422 |
| 9,079,060 | B2 * | 7/2015 | Hong | A63B 71/06 |
| 9,108,098 | B2 * | 8/2015 | Galasso | A63B 24/0021 |
| 9,242,561 | B2 * | 1/2016 | Katayama | B62B 5/0069 |
| 9,259,634 | B1 | 2/2016 | Bouse | |
| 9,421,448 | B2 * | 8/2016 | Tropper | A61B 5/1118 |
| 9,422,018 | B2 * | 8/2016 | Pelot | B62J 1/02 |
| 9,433,552 | B2 * | 9/2016 | Chang | A61H 3/04 |
| 9,789,023 | B1 * | 10/2017 | Lee | A61H 3/00 |
| 9,827,162 | B1 * | 11/2017 | Vidmar | A61H 3/04 |
| 9,849,057 | B1 * | 12/2017 | Janeczek | A61H 3/04 |
| 9,857,025 | B2 * | 1/2018 | Gottinger | F16P 3/08 |
| 2002/0109394 | A1 * | 8/2002 | Phillips | E04G 23/006 299/36.1 |
| 2004/0121700 | A1 * | 6/2004 | Derrah | A63H 13/045 446/154 |
| 2004/0162672 | A1 * | 8/2004 | Kim | G01C 21/3632 701/468 |
| 2004/0224740 | A1 * | 11/2004 | Ball | A63F 13/10 463/6 |
| 2004/0255425 | A1 * | 12/2004 | Arai | A47L 5/28 15/300.1 |
| 2005/0239601 | A1 * | 10/2005 | Thomas | A63B 24/00 482/1 |
| 2006/0082171 | A1 * | 4/2006 | Olmstead | A63B 47/021 294/19.2 |
| 2006/0106496 | A1 * | 5/2006 | Okamoto | G05D 1/0272 700/253 |
| 2006/0166737 | A1 * | 7/2006 | Bentley | A61B 5/1122 463/30 |
| 2006/0204045 | A1 * | 9/2006 | Antonucci | G06K 9/00342 382/107 |
| 2006/0206246 | A1 * | 9/2006 | Walker | G06Q 10/00 701/16 |
| 2007/0078018 | A1 * | 4/2007 | Kellogg | A63B 24/0021 473/151 |
| 2007/0136981 | A1 * | 6/2007 | Dilger | A47L 9/009 15/319 |
| 2007/0269300 | A1 * | 11/2007 | Menard | B62B 3/001 414/444 |
| 2008/0023247 | A1 * | 1/2008 | Hall | B60K 28/14 180/274 |
| 2008/0269016 | A1 | 10/2008 | Ungari et al. | |
| 2008/0276408 | A1 * | 11/2008 | Gilbert, Jr. | A47L 11/34 15/320 |
| 2009/0242285 | A1 * | 10/2009 | Whetstone, Jr. | B62D 49/0692 180/19.2 |
| 2010/0056238 | A1 * | 3/2010 | Terrell, II | A63H 18/00 463/6 |
| 2013/0209979 | A1 * | 8/2013 | Mihelj | A61B 5/11 434/247 |
| 2014/0144467 | A1 * | 5/2014 | Merz | A47L 11/4055 134/6 |
| 2014/0188325 | A1 * | 7/2014 | Johnson | G05D 1/0227 701/26 |
| 2014/0330408 | A1 * | 11/2014 | Rolley | G06F 19/3481 700/91 |
| 2014/0345957 | A1 * | 11/2014 | Bernstein | B60R 11/00 180/21 |
| 2015/0000068 | A1 * | 1/2015 | Tsuboi | A47L 9/009 15/319 |
| 2015/0075575 | A1 * | 3/2015 | Karlovich | A63B 69/0064 135/66 |
| 2016/0027325 | A1 * | 1/2016 | Malhotra | G06F 19/3481 434/252 |
| 2016/0080663 | A1 | 3/2016 | Kelley | |
| 2016/0103451 | A1 * | 4/2016 | Vicenti | G05D 1/0242 700/259 |
| 2016/0292865 | A1 * | 10/2016 | Floor | G06T 7/0042 |
| 2016/0349282 | A1 * | 12/2016 | Gobara | G01C 21/165 |
| 2017/0003111 | A1 * | 1/2017 | Coza | G01B 7/003 |
| 2017/0303825 | A1 * | 10/2017 | Martinson | A61B 5/112 |

OTHER PUBLICATIONS

European Search Report for corresponding European Patent Application No. 17193112.4, European Patent Office, Munich, Germany, dated Feb. 16, 2018.

(56) References Cited

OTHER PUBLICATIONS

Nimmons, Steve, "Sports Performance, Biotelemetry and Robotics," EA Voices, <https://eavoices.com/2014/03/06/sports-performance-biatelemetry-and-robotics/>, dated Mar. 6, 2014.
Moran, Emily, "Meet Moses Frenck, the Man Who Wants to Bring Drones to Your School's Practice Field," Stack, <http://www.stack.com/a/moses-frenck-aerotrainer-sports-drone>, dated Apr. 3, 2014.
Wade, Alison, "Could Your Next Running Partner Be a Drone?," Runner's World, <http://www.runnersworld.com/general-interest/could-your-next-running-partner-be-a-drone>, dated May 18, 2015.
Beer, Jeff, "Puma Created a Robot as Fast as Usain Bolt to Make Athletes Better," Co.Create, <https://www.fastcocreate.com/3059417/puma-created-a-robot-as-fast-as-usain-bolt-to-make-athletes-better>, dated Apr. 29, 2016.
"Nike Chalkbot," Deeplocal, <http://www.deeplocal.com/projects/chalkbot.html>, accessed Jun. 14, 2017.
José Jair Alves Mendes Jr. et al., Sensor Fusion and Smart Sensor in Sports and Biomedical Application, Sensors 2016, 16, 1569; doi:10.3390/s16101569, www.mdpi.com/journal/ sensors, 31 pages.
John Patrick V. Azcueta et al., In Situ Sports Performance Analysis System Using Inertial Measurement Units, High-FPS Video Camera, and the Android Platform, 7th IEEE International Conference Humanoid, Nanotechnology, Information Technology, Communication and Control, Environment and Management (HNICEM), The Institute of Electrical and Electronics Engineers Inc. (IEEE)—Philippine Section, Nov. 2-16, 2013 Hotel Centro, Puerto Princesa, Palawan, Philippines, 6 pages.

\* cited by examiner

ROBOTIC TRAINING SYSTEMS AND METHODS

FIELD OF THE INVENTION

Embodiments of the present invention generally relate to systems and methods for using robotics to assist an individual in improving a workout. More particularly, robotic systems and methods may be used as coaching tools, guides, and/or pace setting systems.

BACKGROUND OF THE INVENTION

Athletic activity is important to maintaining a healthy lifestyle and is a source of entertainment for many people.

Individuals engaged in athletic activities have sought aids to help with pacing and coaching during running workouts. Typical methods include running on circular tracks of known lengths and employing a stop watch to record intervals or calculate speed. When a running event, such as a race, requires assistance to set a particular pace, other runners may be enlisted to aid in the effort and maintain a consistent pace. In a race environment these runners may be called "rabbits" and are often paid to run only a portion of the race to ensure a fast opening pace.

In more recent years runners have employed additional tools in an effort to assist in tracking and coaching workouts. For example, GPS and accelerometer based devices may be used to provide speed and distance information. Fitness monitoring devices have also been developed that are capable of recording information about an individual's performance during an athletic activity using sensors, and in some cases providing feedback about the individual's performance. Some fitness monitoring devices employ sensors attached to the individual's body, while other fitness monitoring devices rely on sensors attached to a piece of athletic equipment. Such sensors may be capable of measuring various physical and/or physiological parameters associated with the individual's physical activity.

An individual engaged in an athletic activity—or an interested observer such as a coach or fan—may desire to receive information about the athletic activity, including information about the individual's performance. But with respect to providing this information, existing athletic/fitness activity monitoring, training, and coaching systems suffer from a number of drawbacks. Many existing systems are limited in the amount of feedback or coaching that they can give. Other systems may provide coaching feedback during the activity, but in a way that distracts that individual or interested observer from focusing on the ongoing athletic activity itself. And many existing systems do not provide physical targets for individuals to react to, or an adequate substitute for a training partner. These systems are not suitable for monitoring in many real world athletic competitive or training sessions. Finally, existing athletic activity monitoring, training, and coaching systems often fail to provide the individual or interested observer with quick, accurate, insightful information that would enable them to easily compare past performances, develop strategies for improving future performances, or visualize performances.

BRIEF SUMMARY OF THE INVENTION

What is needed are athletic activity training, and coaching, systems and methods having improved capabilities over existing systems, thus offering individuals engaged in athletic activities and other interested observers better tools to improve their performance through coaching feedback. At least some of the embodiments of the present invention satisfy the above needs and provide further related advantages as will be made apparent by the description that follows.

Embodiments of the present invention relate to a robotic training system, for example, an athletic training system for assisting an individual during an athletic activity in an environment. The system may include a mobile robotic platform, a sensor module including an array of optical sensors coupled to the mobile robotic platform and configured to obtain sensor data from the environment, a drive system configured to propel the mobile robotic platform, a steering system configured to steer the mobile robotic platform, and a processor. The processor may be configured to receive the sensor data from the sensor module, characterize the sensor data into one of edge data, color data, saturation data, threshold data, or keypoint data, and to control one of the drive system and the steering system to follow a path based on the characterized data. The sensor data comprises data related to variation of a surface of the environment.

Embodiments of the present invention also relate to a robotic training system, for example, an athletic training system for assisting an individual during an athletic activity in an environment. The system may include a mobile robotic platform, a sensor module including an array of sensors coupled to the mobile robotic platform and configured to obtain data from the environment, a drive system configured to propel the mobile robotic platform, a steering system configured to steer the mobile robotic platform, and a processor. The processor may be configured to receive the data from the sensor module and to control one of the drive system and the steering system to follow a path based on the data. The data may include data related to variation of a surface of the environment.

Embodiments of the present invention also relate to a method of training an individual, for example, assisting an individual during an athletic activity in an environment using a robotic athletic training system. The method may include controlling the robotic athletic training system with a processor of the robotic athletic training system to move the robotic athletic training system at a velocity, receiving data related to a surface of the environment over which the robotic athletic training system moves and on which the individual conducts their athletic activity with a vision system of the robotic athletic training system, comparing baseline possible surface characteristic data to the received surface data with the processor of the robotic athletic training system, and adjusting a travel direction of the robotic athletic training system in response to the comparison.

Additional features of embodiments of the invention will be set forth in the description that follows, and in part will be apparent from the description, or may be learned by practice of the invention. Both the foregoing general description and the following detailed description are exemplary and explanatory and are intended to provide further explanation of the invention as claimed.

BRIEF DESCRIPTION OF THE DRAWINGS/FIGURES

The accompanying figures, which are incorporated herein, form part of the specification and illustrate embodiments of the present invention. Together with the description, the figures further serve to explain the principles of and to enable a person skilled in the relevant arts to make and use the invention.

Figure 10:
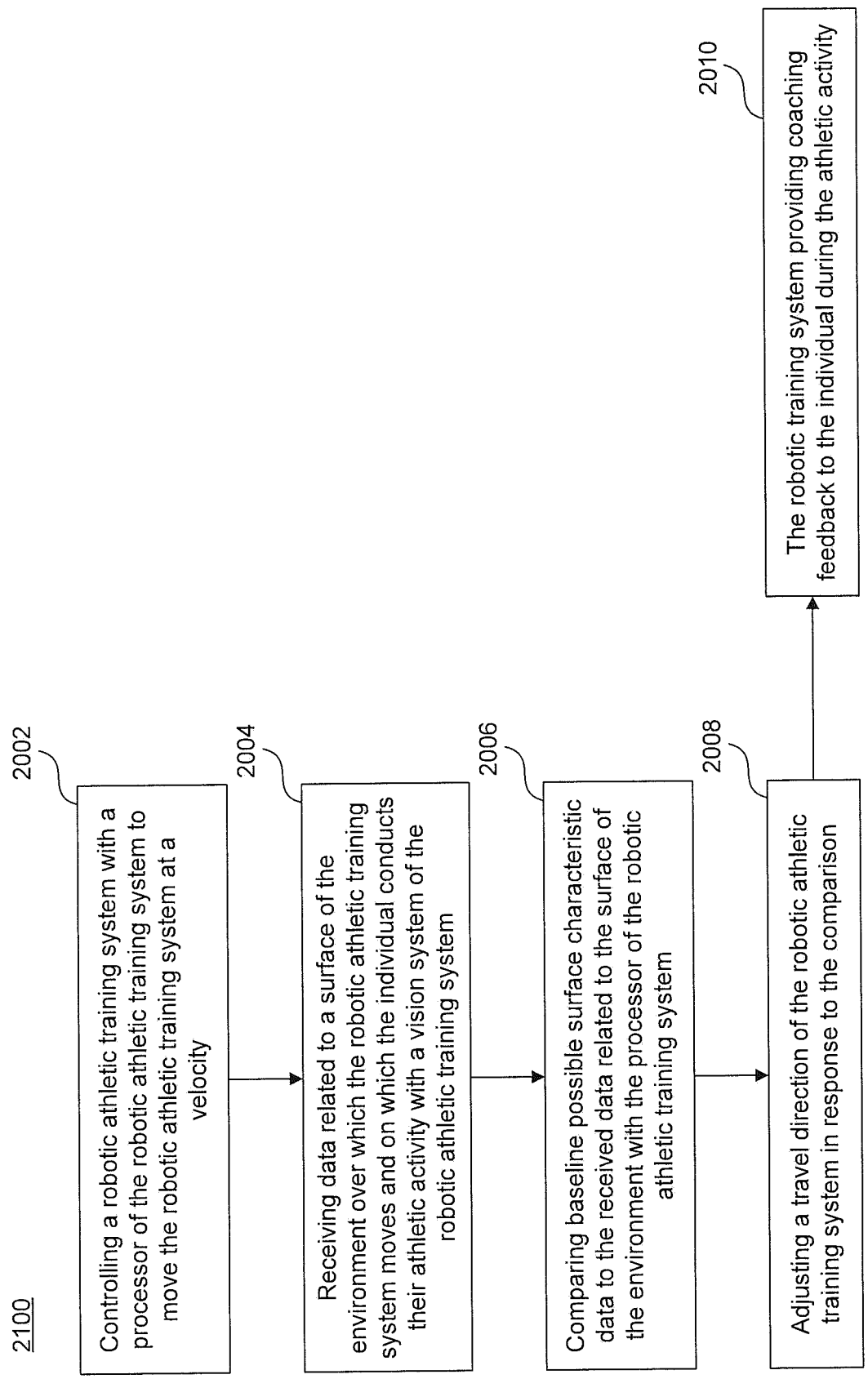
Figure 11:
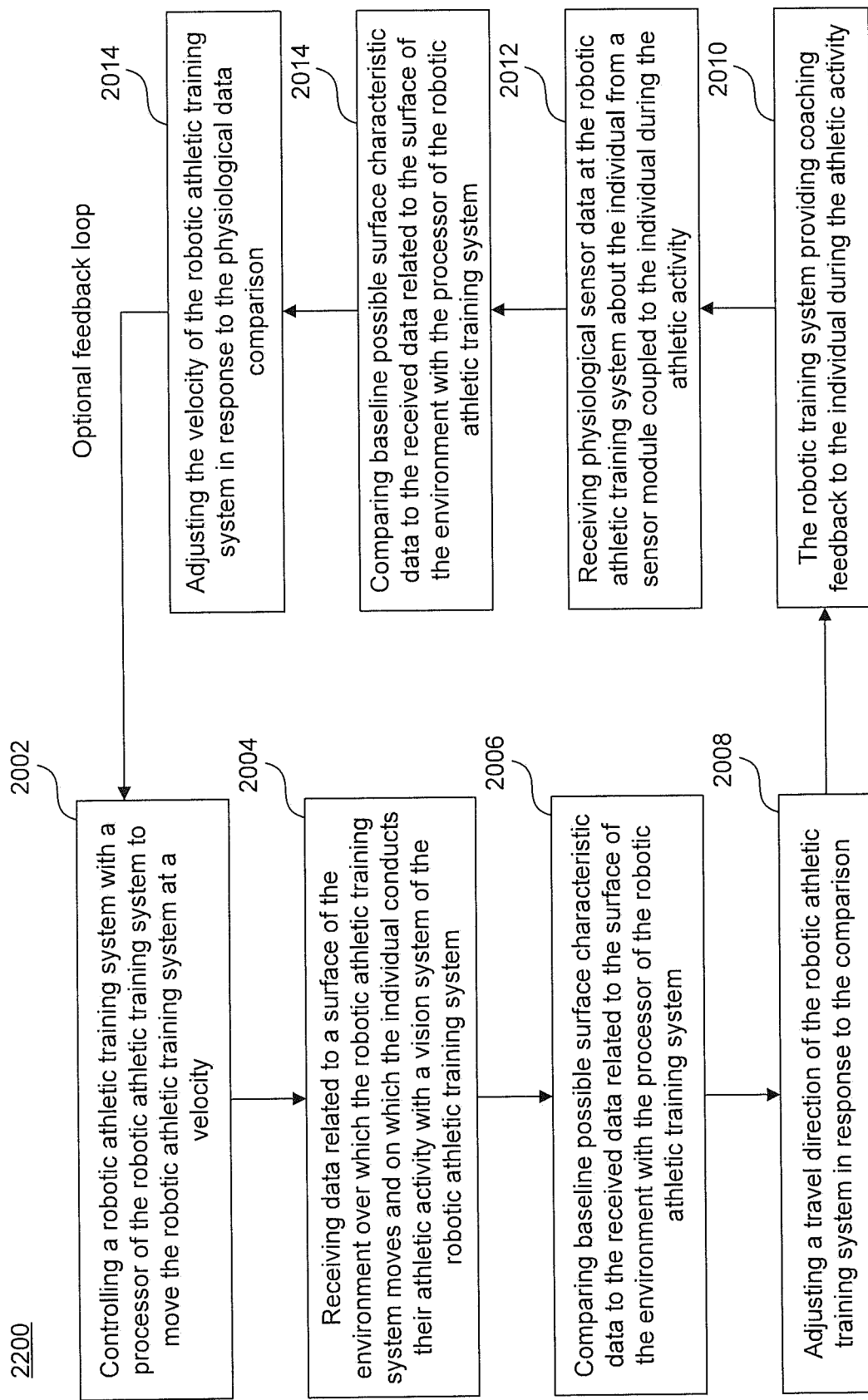

FIG. 10 is a flowchart of a method of assisting an individual during an athletic activity in an environment using a robotic athletic training system according to an embodiment of the present invention FIG. 11 is a flowchart of a method of assisting an individual during an athletic activity in an environment using a robotic athletic training system according to an embodiment of the present invention

DETAILED DESCRIPTION OF THE INVENTION

The present invention will now be described in detail with reference to embodiments thereof as illustrated in the accompanying drawings. References to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, non-transitory tangible computer readable or computer usable storage media having instructions stored thereon, or a combination thereof, and may be implemented in one or more computer systems or other processing systems.

The methods and systems discussed above are further described below. The figures below may apply to both the method and system embodiments of the invention.

In general, in some embodiments, systems and methods are provided to enhance athletic training. The robotic platforms described herein may be autonomous or semi-autonomous small-scale vehicles. The systems and methods may, for example, follow the lanes of a running track, and may be used as a virtual coach by providing audio, visual display and haptic feedback to runners and can instruct them to speed up or slow down to meet a specific goal of the run. Additionally, they may be used to set pacing for a runner, coach an individual through different workout intervals, collect athletic data, and record video for gait and/or technique analysis.

Advantageously, as opposed to audio or video simulations, the robotic training systems and methods may give runners a tangible target to focus their workouts. This may advantageously improve the quality of feedback, for example, by having the robotic training system gradually accelerate/decelerate. This is in contrast to coaching being given as discrete, separate steps, in order to avoid over instructing the individual (e.g., change pace to 8 minutes per mile, prepare to run a 30 second interval at maximum speed, etc.). Additionally, rather than telling the individual to accelerate to a certain pace or zone, the robotic training system may simply show them the pace through its motion. In some embodiments, robotic training system may adjust to the individual's ability (e.g., if the individual can't keep up the robotic training system may adjust the pace or direction). Advantageously, the individual engaged in athletic activity is able to keep their eyes focused on the robotic training system in front of them instead having to look down at a wrist band, phone, etc., which could dangerously divert their eyes from the route in front of them. Additionally, being able to focus generally in front of the individual, rather than raising an arm or looking down, avoids introducing inefficient body positioning or form into the athletic activity.

In addition, the robotic training system may provide for more granular training/coaching. For example, the robotic training system may change velocity at a more frequent interval, e.g., by speeding up or slowing down gradually and having an individual follow the pace. Disadvantageously, other coaching methods attempting to verbally instruct an individual through granular or widely varying velocity risk over-coaching and overwhelming the individual.

Substantially real time feedback may also be provided by the robotic training system. GPS and accelerometer systems may include lags in reporting changes of speed. In contrast, the robotic training system embodiments of the present invention may instead utilize on board speed sensors (e.g., rotational speed sensors) and may use, for example, visual sensors focused on the individual in combination with the robotic training system's speed to adjust the operation of the system.

As shown in FIGS. 1-4, in some embodiments, robotic training system 10 may include a mobile robotic platform 100, a sensor module 102, a drive system 104 configured to propel mobile robotic platform 100, a steering system 106 configured to steer the mobile robotic platform 100, and a processor 110. Processor 110 may be configured to receive data (e.g., sensor data) from the sensor module and control the drive system 104 or steering system 106 to follow a predetermined path based on the data received from the sensor module 102. Robotic platform 100 may include a frame, housing, etc., that may support or house various components of system 10.

Figure 2:
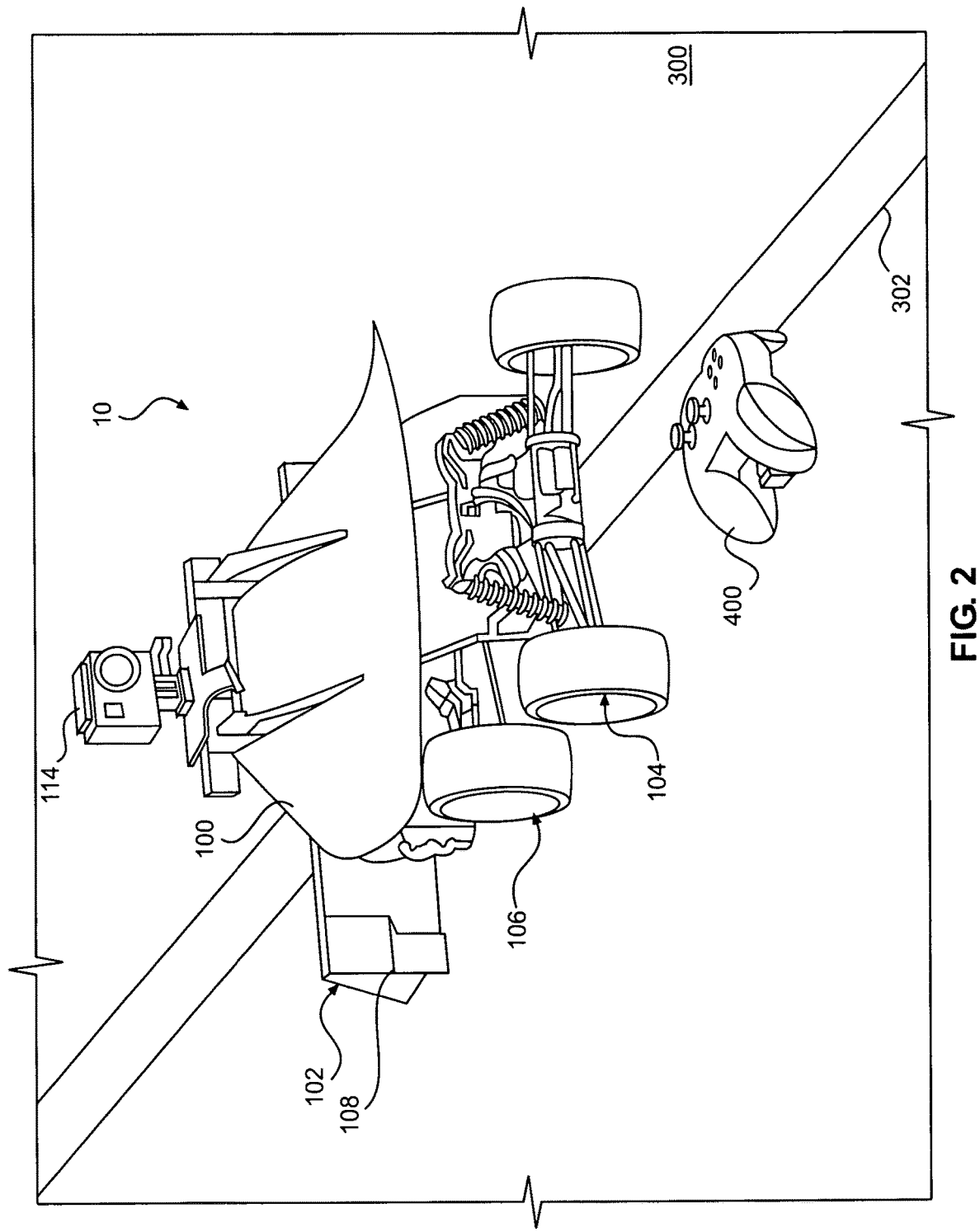
FIGS. 2-3 are illustrations of selected robotic training systems according to embodiments of the present invention.
Figure 3:
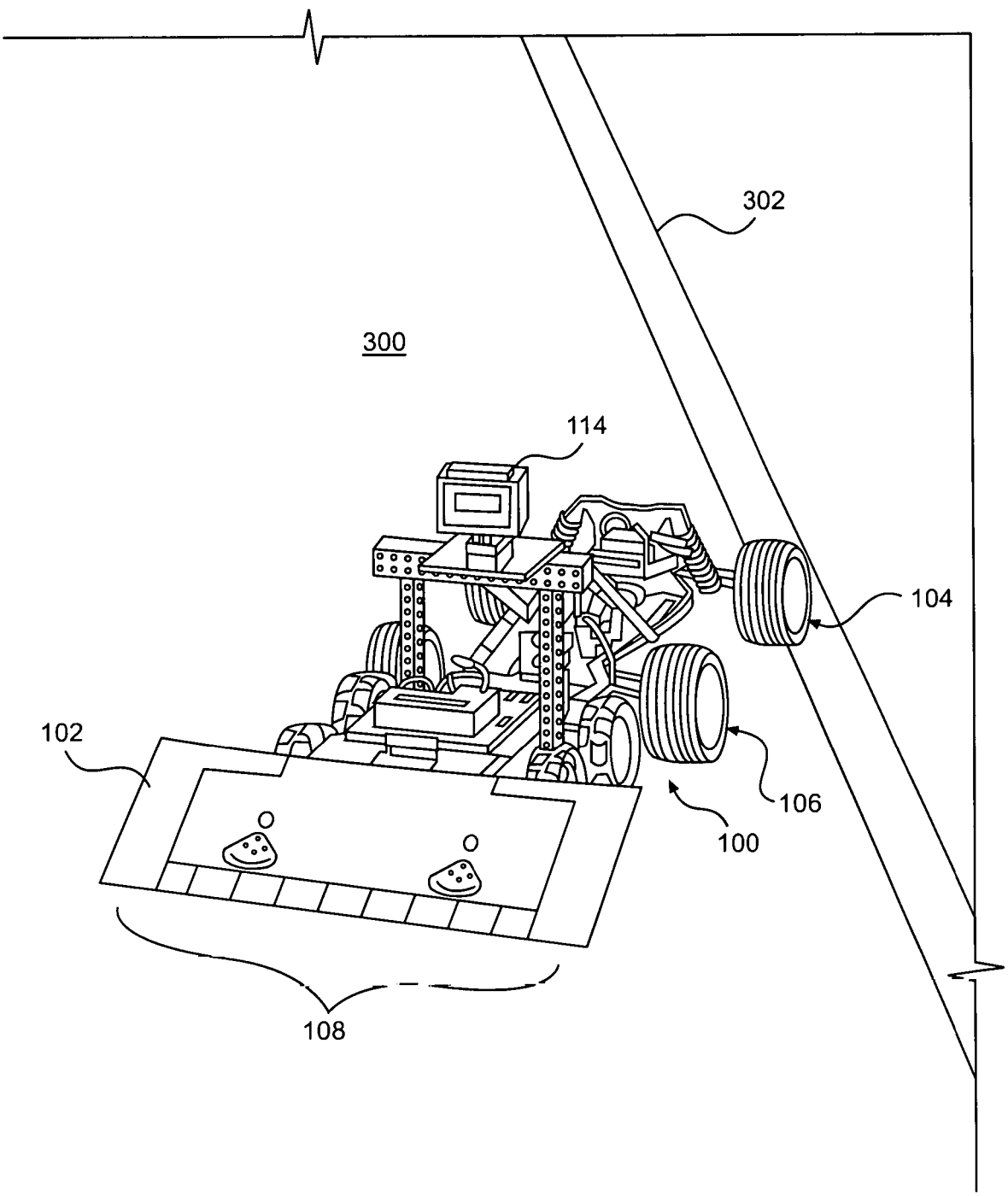

In some embodiments, a predetermined path may be, for example, an athletic track 300, or a paint or chalk line 302 denoting a lane on track 300, as shown in FIGS. 2 and 3. In some embodiments, sensor module 102 may be associated with mobile robotic platform 100 and configured to obtain data from an environment.

Figure 4:
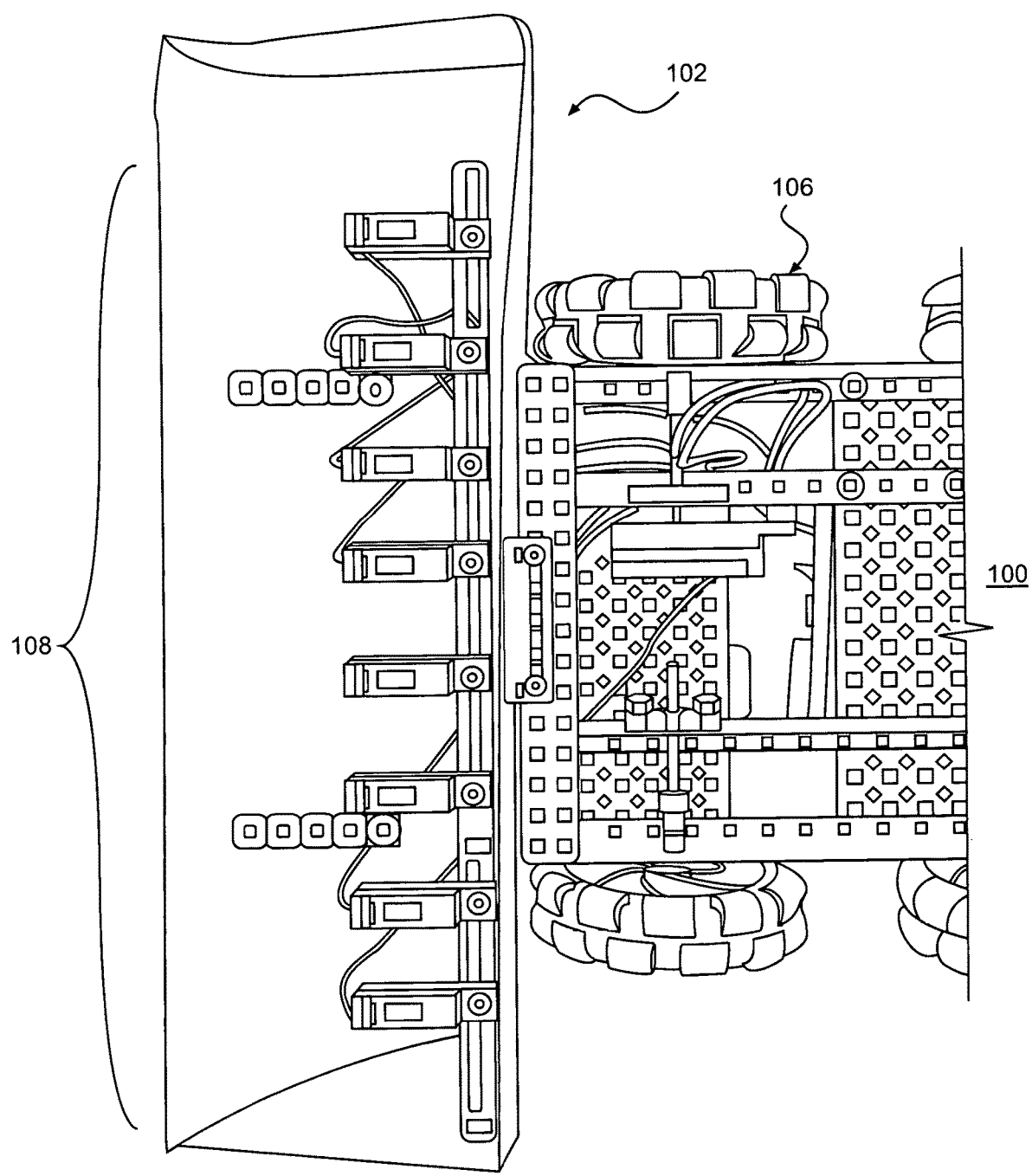
FIG. 4 is an enlarged view of a sensor array according to an embodiment of the present invention.

In some embodiments, sensor module 102 may include an array of sensors 108, as shown, for example, in FIG. 4. In some embodiments, the sensors 108 may obtain data related to variation of a surface, such as an athletic track. In some embodiments, sensors 108 may be positioned in a generally linear arrangement, such that sensors are parallel to one another and the direction of a linear axis about which the sensors are aligned extends is generally perpendicular to the sensed portion of the paint/chalk line 302 during use. In other embodiments, the sensor array may be arranged in a "V" formation as with a group of migratory birds, or in a curved arrangement. In some embodiments, the sensors of the array may be arranged in an offset fashion where they are not parallel to one another.

The sensed surface variation data may be optical data, for example, data related to the relative position or composition of the paint or chalk line denoting a line on track 300. In some embodiments, the sensed data (e.g., optical data) may be characterized and/or quantified to identify certain features, such as edge data, color data, saturation data, threshold data, keypoint data, and the like. In some embodiments, these features may be configured to control the drive or steering systems 104/106. In some embodiments, the sensors transmit data to processor 110, with the processor being further configured to adjust the drive system 104 or steering system 106 based on the data. For example, in some embodiments the sensor array may include an array of sensors (e.g., infrared or "IR" sensors, photo-sensitive systems, CCD, CMOS, etc.), and transmit data related to which sensor is positioned over the paint or chalk line 302 denoting a lane on a track 300. Paint of chalk line composition, line edge relative angles, or other features may be detected. Speed or direction adjustments of the drive system 104 or steering system 106 may vary according to how many sensors sense the presence of the line, frequency of the frame rate, resolution of the captured data, or the relative angle of the edge of the line with respect to one or more sensors, for example. In some embodiments, speed or direction adjustments may vary according to the location of the sensor along the array that senses the presence of the line. In some embodiments, speed or direction adjustments may vary according to a predetermined threshold of time a particular sensor senses the presence of the line. In some embodiments, sensor position, time, or number of sensors sensing the presence of the line may vary the speed and/or direction.

Existing athletic training systems lacking tangible targets—or systems that rely on tangible targets that unable to accurately sense track surface conditions and respond accordingly—disadvantageously may not provide a suitable level of natural, smooth feedback and coaching to the individual. In contrast, the robotic training system 10 of the present invention employing embodiments of sensor module 102 may provide natural, smooth feedback and coaching based on real world track surface conditions.

In some embodiments drive system 104 and/or steering system 106 may be, for example a wheeled system. In some embodiments, these systems may be a track system, an aerial propulsion system, a magnetic propulsion system, a rail system, a robotic leg system, or other suitable drive system. In some embodiments, the drive system 104 and steering system 106 may be autonomous, or semi-autonomous. Autonomous or semi-autonomous systems may have advantages over known systems that rely on significant user or coach input or control, which may be more cumbersome to control and may limit their use. In some embodiments, robotic platform 100 may include a frame configured to support athletic equipment or supplies (e.g., used as a type of robotic "pack mule"). For example, some embodiments may be specifically configured to carry and/or dispense water, food, or first aid equipment.

In some embodiments, additional sensor modules 102 may be employed, either physically integrated with robotic platform 100 or separate from robotic platform. In some embodiments, sensor modules 102 may include additional sensors, for example, physiological sensors or the like.

In some embodiments, system 10 may be partially or wholly solar powered, which may advantageously extend the range of the device of limit the need for frequent charging or battery replacement.

In some embodiments, system 10 may further include a wireless transceiver 112 in communication with an electronic device 400 associated with an individual 500. In an embodiment, the electronic device 400 may be, for example, a smart phone, a smart watch, a heads-up-display device, other smart apparel, a tablet, or any other type of suitable mobile computing device. In some embodiments, transceiver 112 may receive data (e.g., electronic device data, or input data) from electronic device 400, transmitting that data to processor 110. In some embodiments, processor 110 adjusts the drive system 104 or steering system 106 based on the data received from electronic device 400. In some embodiments, the transceiver 112 receives data including programmed instructions to control the drive and steering systems 104/106 according to a workout program. In this way, embodiments including a communication with an electronic device 400 may advantageously allow for a higher level of accuracy or customization in the performance of the robotic training system 10. In some embodiments, electronic device 400 may function as a sensor module 102.

In some embodiments, these programs could include instructions to provide coaching feedback to individual 500 during a workout, for example, a training run. In some embodiments, individual 500 may receive coaching instruction, for example, or encouragement. In some embodiments these programs may include a simulated race, where robotic platform 100 may be programmed with prior race data such that it moves according to a race pace and individual 500 may attempt to beat the platform. In some embodiments, these programs may include world record data, such that individuals 500 may "compete" against current world records. Transceiver 112 may be integral with robotic platform 100, or may be a separate unit. Additional details of the software platform and modules related to such programs along with programs and functions of the components are further discussed herein.

Figure 5:
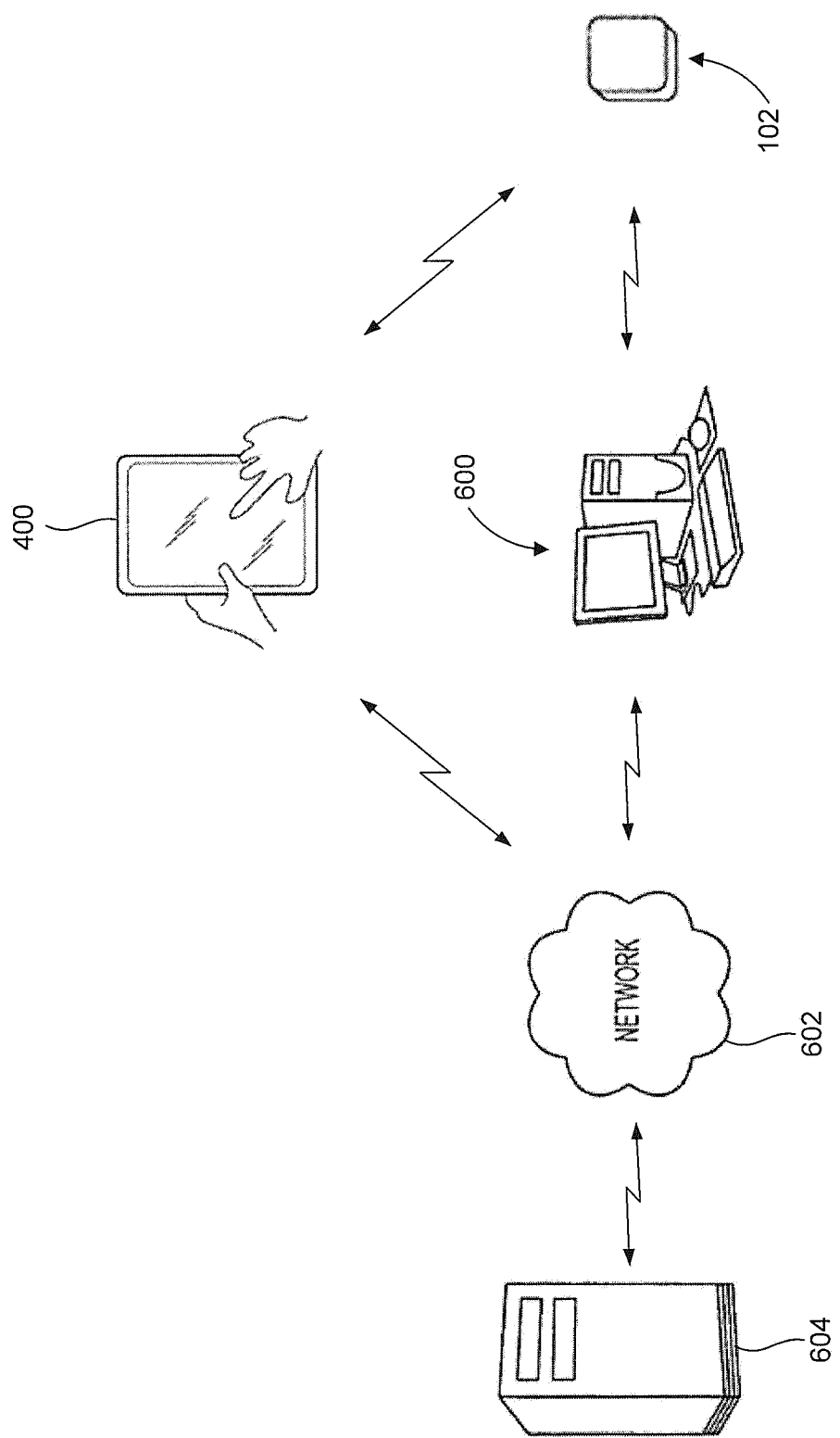
FIG. 5 is a diagram of a sensor module interacting with one of an electronic device, a standalone device, a network, and a server according to an embodiment of the present invention.

Transceiver 112 may allow sensor module 102 to communicate, for example, with other locally or remotely located robotic platforms 100, or other standalone devices 600, via network 602, or server 604, for example, as shown in FIG. 5. Communication between these components may be one way communication or two way communication.

In some embodiments, system 10 may include a user interface configured to receive input data and transmit the data to processor 110 which may adjust the drive or steering systems 104/106 based on the input data. In some embodiments, the user interface may be displayed on electronic device 400, for example, or may be integrated directly into robotic platform 100.

Figure 1:
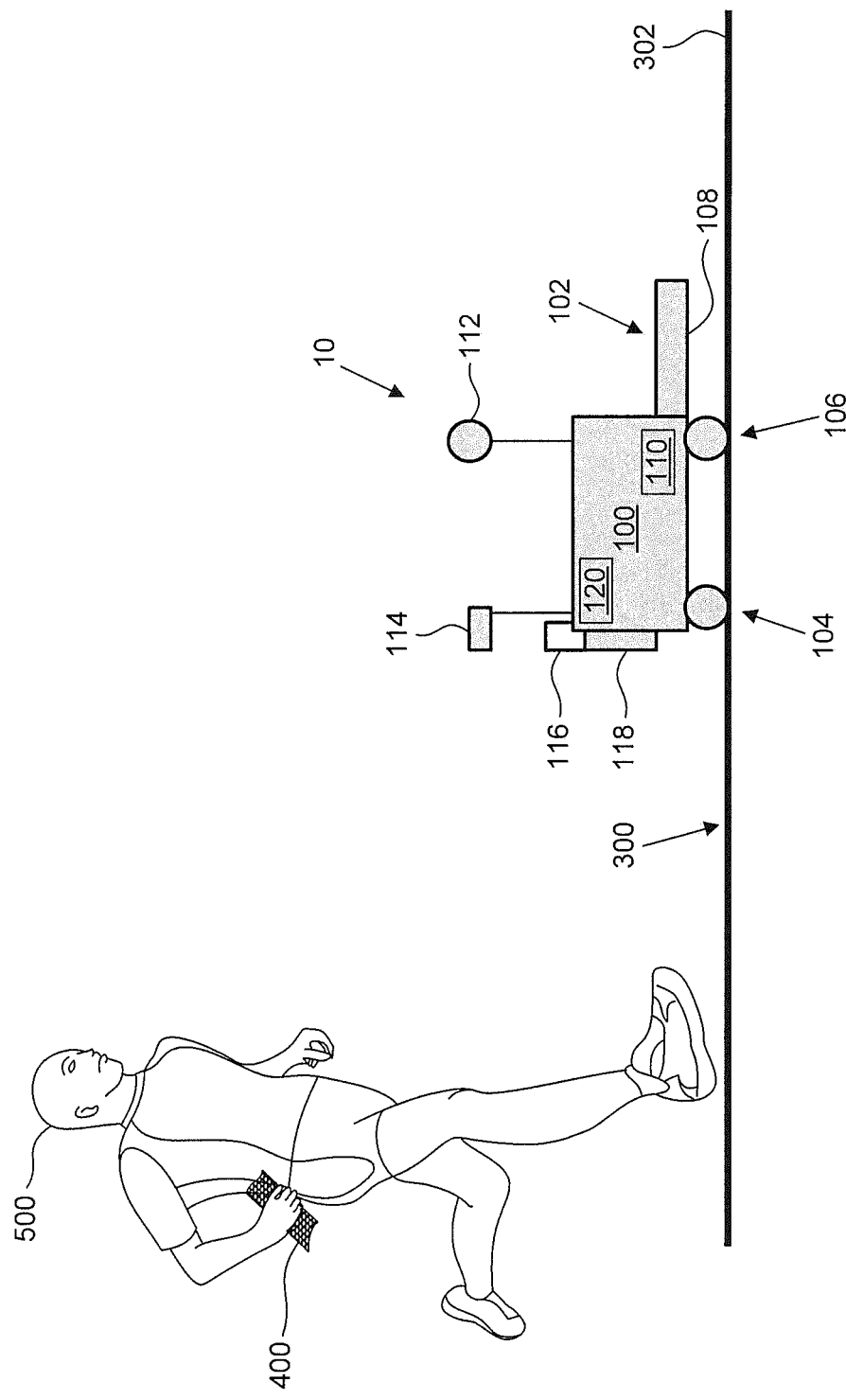
FIG. 1 is an illustration of an individual using a robotic training system according to an embodiment of the present invention.

As shown in FIGS. 1-3, for example, in some embodiments, system 10 may include a video camera 114. Video camera 114 may be configured to record an individual during training, for example. In some embodiments, video camera 114 may transmit video data to processor 110. In some embodiments, processor 110 is configured to analyze physiological characteristics of the individual (e.g., analyze gait or foot strike characteristics, analyze other running form characteristics, recognize onset of fatigue, recognize perspiration levels, etc.). In some embodiments, video camera 114 may be configured to record the surface an individual is running on, for example, or capture video of environmental surroundings. In some embodiments, processor 110 may analyze, for example, gait characteristics such as foot strike type (e.g. heel, midfoot, forefoot, etc.), rate of pronation or supination, and degree of pronation and supination. In other embodiments, video camera 114 may be configured to record the path ahead of the individual during training so as to record a first person-style view of the route traversed by the robotic training system 10 and the individual. In other embodiments, the video camera 114 may pan around the environment to record video of competitors, spectators, or other items of interest. The panning may be autonomous or controlled by the individual or a third party such as a coach.

In some embodiments, additional robotic platforms 100 may be able to interact with one another based on sensor feedback. For example, in some embodiments, a land based robotic platform 100 may carry out training feedback functions to the individual 500, while an aerial based robotic platform 100 may include video camera 114 and carry out aforementioned video functions, based upon position of the land based robotic platform 100 or individual 500, for example.

In some embodiments, system 10 may include an audio feedback system 116. In some embodiments, audio feedback system 116 is configured to provide information about a workout to an individual during the workout. In some embodiments, audio feedback system 116 may provide audio coaching, for example to alert individual 500 to a change in the workout, to accelerate/decelerate, alert individual 500 of other individuals approaching, or to alert of other robotic platforms 100 (e.g., to urge slower runners to move to the right). Combined audio and visual feedback may enhance the coaching of an individual, as it more closely replicates one-on-one coaching between individuals, rather than an individual following only audio prompts. In some embodiments, audio feedback system 116 may be configured to allow, for example, one-on-one coaching feedback from an individual's coach, in addition to feedback from the system 10.

In some embodiments, system 10 may include a display system 118. Display system 118 may be, for example, a projector, display screen, laser system, holographic display, paint/chalk display system, or the like. In some embodiments, display system 118 is configured to provide information about a workout to an individual during the workout or other information or visual cues (e.g., display image on track or body of robotic platform 100, display a line to follow, follow distance, or workout details). In some embodiments, display system 118 may display visual cues, such as time remaining, current speed, number of laps, etc. In some embodiments, display system 118 may allow for video calling other individuals (e.g., friends or competitors). In some embodiments, display system 118 may include a heads up display (HUD), for example, on a helmet, or electronic eyeglasses. In some embodiments, the display system 118 may project information or images on the surface of the track ahead of the individual and/or ahead of the robotic training system 10, which may advantageously allow the individual to visual receive information without having to divert their field of view of otherwise break their form to view a display on a smartphone, smart watch, or other portable display. In some embodiments, a display mounted on the robotic training system 10 itself may provide a similar benefit.

In some embodiments, system 10 may include an audio input system 120. Audio input system 120 may be configured to accept audio data and transmit the data to the processor to control system 10. In some embodiments, audio input system 120 may function as a voice control/recognition system, and accept information such as individual 500 speaking commands to speed up or slow down, provide navigation, place an emergency call, place a call to a coach or trainer, place a video call to other individuals (e.g., friends or competitors), or post an update on a social media platform.

Some embodiments are directed to a method of training including initiating programming data such that a robotic training system moves at a predetermined velocity, wherein the robotic training system includes a vision system configured to receive data related to a surface, receiving data related to a surface, comparing a baseline data of a desired surface to the received data, and adjusting a travel direction of the robotic system in response to the comparison. In some embodiments, the data received related to a surface is optical data indicating the position of a line on a track. Existing systems often do not account for surface variation (e.g., if an individual begins running on a track but transitions to a grass field). In contrast, embodiments of the present invention may provide variation in coaching feedback depending upon the surface upon which the athletic activity is performed (e.g., a field, artificial turf, track, sidewalk, etc.).

Figure 9:
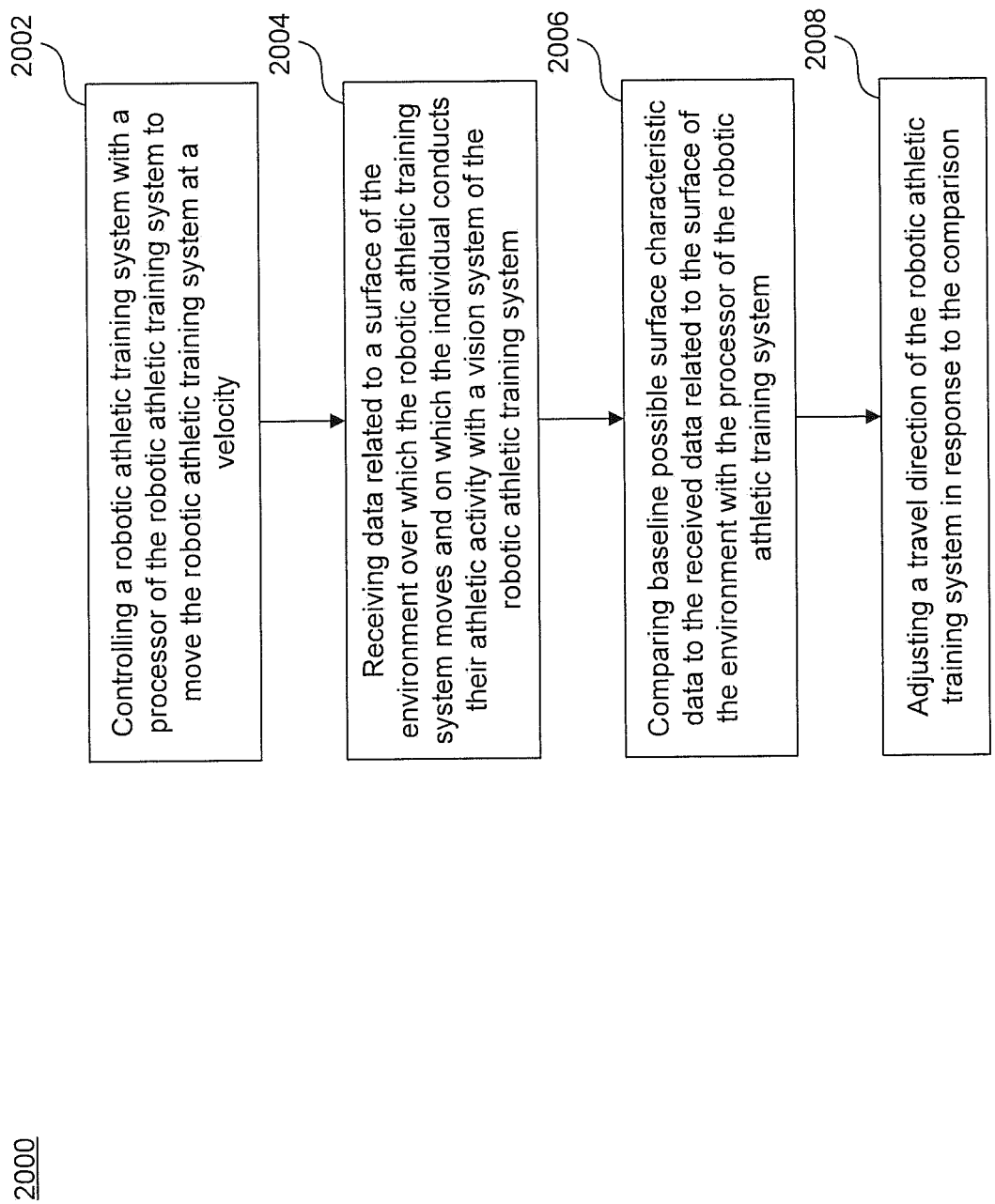
FIG. 9 is a flowchart of a method of assisting an individual during an athletic activity in an environment using a robotic athletic training system according to an embodiment of the present invention.

Turning to an exemplary method 2000 shown in FIG. 9, at step 2002, the method may include controlling a robotic athletic training system with a processor of the robotic athletic training system to move the robotic athletic training system at a velocity. The method may then include receiving data related to a surface of the environment over which the robotic athletic training system moves and on which the individual conducts their athletic activity with a vision system of the robotic athletic training system at step 2004, comparing baseline possible surface characteristic data to the received data related to the surface of the environment with the processor of the robotic athletic training system at step 2006, and adjusting a travel direction of the robotic athletic training system in response to the comparison at step 2008.

Exemplary method 2100 shown at FIG. 10 may include each of the steps shown in method 2000. Further, the method may include the robotic training system providing coaching feedback to the individual during the athletic activity at step 2010.

Exemplary method 2200 shown at FIG. 11 may include each of the steps shown in methods 2000 and 2100. Additionally, the method may include receiving physiological sensor data at the robotic athletic training system about the individual from a sensor module coupled to the individual during the athletic activity at step 2012, comparing baseline possible surface characteristic data to the received data related to the surface of the environment with the processor of the robotic athletic training system at step 2014, and adjusting the velocity of the robotic athletic training system in response to the physiological data comparison at step 2016. Additionally, each of the methods may include an optional feedback loop from either step back to any previous step.

It should be understood that the order of the operations listed above is exemplary. The order of the operations may be rearranged and some operations may be omitted.

In some embodiments, the method further includes receiving physiological sensor data at a robotic training system 10 about an individual 500 from a sensor module associated with the individual 500 during an athletic activity engaged in by the individual. In some embodiments, the method includes comparing the physiological sensor data received to baseline physiological data using a processor (for example processor 110), and adjusting the programming data based on the comparison such that the velocity (or direction) of the robotic training system is adjusted. In some embodiments, the method further includes receiving personal information about the individual prior to receiving the physiological data. In some embodiments the personal information includes one of prior injury information, height, weight, gender, an athletic goal, intended athletic environment, intended athletic duration, intended workout intensity.

The system or method may include receiving data about the individual from a sensor module associated with the individual during a first athletic activity engaged in by the individual. The method may also include receiving data about the individual from the sensor module associated with the individual during a second athletic activity engaged in by the individual, and determining a second characteristic based on the data related to the second athletic activity. The method may also include comparing the data received during the first/second athletic activities; and providing a recommendation about a workout.

In some embodiments, the first and second data received may include physiological characteristics (e.g. respiratory or cardiac data). In some embodiments, the method may determine whether a characteristic of the second data represents an improvement over the first data. In some embodiments, the method may include receiving data (e.g., motion data, physiological data, etc.) via local wired or wireless connection, or via a wide area network. In some embodiments, the method may include monitoring the motion of an individual in substantially real-time during an athletic activity. In some embodiments, a sensor module 102 may be provided and configured to obtain data relating to a physiological parameter of the individual 500 during an athletic activity.

Figure 6:
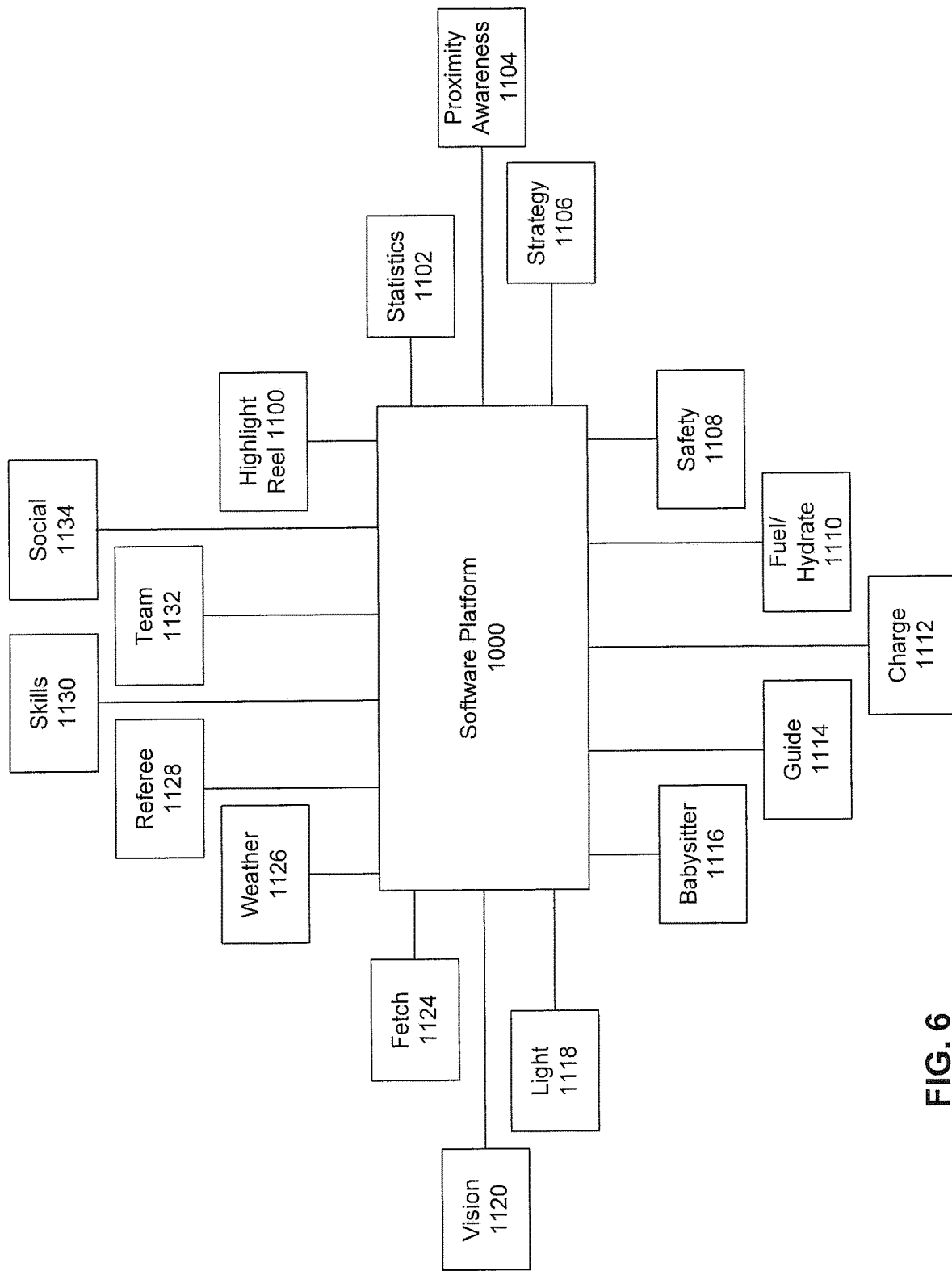
FIG. 6 is a conceptual diagram of a software platform and software modules, according to an embodiment of the present invention.

The systems and methods may be effected through software platform 1000 (which may be included in system 10), containing software modules, as shown in FIG. 6, for example. In some embodiments, fewer modules may be included, or additional modules may be included. In some embodiments, modules may be removed or added, for example through a network connection. Programming data may include software platform 1000, for example, as shown in FIG. 6, and include various modules. Each of the components in sensor module 102, for example, or electronic device 400, may feed the modules data that the modules use to formulate a response. In some embodiments programming data includes simulated race data such that the robotic training system moves at a race pace. In some embodiments, the programming data includes feedback data such that the robotic training system provides coaching feedback to an individual during a workout. In other embodiments, the systems and methods may be effected through software platform 1000 in an electronic device 400 in addition to or instead of in system 10.

As shown in FIG. 6, software platform 1000 may include highlight reel module 1100, including programming to capture video data from video camera 114 and compose a video montage or highlight reel.

In some embodiments, software platform 1000 may include a statistics module 1102. Statistics module 1102 may be programmed to display relevant statistics regarding the workout such as distance, time, pace, heart rate, physiological data, etc. In some embodiments, statistics module 1102 may function as a workout coach, by providing instructions or feedback through display system 118 or audio feedback system 116. In some embodiments, statistics module 1102 may include a lap counter, for example, in order allow an individual to run accurate distances in any lane.

In some embodiments, software platform 1000 may include a proximity awareness module 1104. Proximity awareness module 1104 may use additional sensor data (or data from sensor module 102) to guide robotic platform 100 around obstacles, for example, or to maintain a safe distance from an individual 500 using system 10. In some embodiments, proximity awareness module 1104 may notify an individual running of other runners near the individual, or aware of other competitor's status in a race event, for example. In some embodiments, proximity awareness 1104 module may optimize a route, for example, accounting for particular surfaces or geography, or may analyze a route taken by an individual (e.g., how an individual approaches corners, etc.). In some embodiments, proximity awareness module 1104 may communicate with other robotic platforms 100. In some embodiments, proximity awareness module 1104 may include, for example a radar system or ultrasonic system with radar sensors or ultrasonic sensors.

In some embodiments, software platform 1000 may include a strategy module 1106. Strategy module 1106 may include instructions to coach an individual for particular conditions (e.g., coaching a runner to slow down while traveling uphill or into headwind and accelerate for downhill or tailwind). Strategy module 1106 may use data from sensor module 102, for example vision sensor data, or additional sensor data, such as proximity sensor data. In some embodiments, strategy module may coach the individual to adjust their performance, for example adjusting their gait, stride, or posture for different terrain (e.g., going uphill or downhill). In some embodiments, data from video camera 114 may be used as an input to strategy module 1106 and coaching may be dependent upon video data analysis (e.g., fatigue or gait analysis).

In some embodiments, software platform 1000 may include a safety module 1108. Safety module may, for example, coach an individual running to slow down when approaching uneven or dangerous surface conditions, or when physiological data reaches unsafe levels. In some embodiments, safety module may control driving or steering system 104/106 to avoid obstacles or brake if communication or other signals are lost or are abnormal. In some embodiments, safety module may leave individual 500 and dial an emergency number if cellular coverage is unavailable. In some embodiments, safety module 1108 may utilize data from sensor module 102 to maintain a predetermined position around individual 500, for example ahead, behind, or beside individual 500. In some embodiments, safety module 1108 calculates an acceptable radius from individual 500 and adjusts based upon the path taken by individual 500. In some embodiments, safety module 1108 may for example, pick up litter after a race along a race path.

In some embodiments, software platform 1000 may include a Fuel/Hydrate module 1110. Fuel/Hydrate module 1110 may utilize workout data, data from sensor module 102, etc., to coach individual 500 on proper food and water intake during a workout. In some embodiments, robotic platform 1000 may include on board fluid and food to provide to individual 500. In some embodiments, Fuel/ Hydrate module 1110 may include a mist function, for example, if it is hot outside, or if individual 500 reaches a predetermined temperature as measured by sensor module 102.

In some embodiments, software platform 1000 includes Charge module 1112. Charge module 1112 may provide an energy source for long races to charge a phone, for example as electronic device 400. Charge module 1112 may activate, for example, Bluetooth charging when electronic device 400 charge level falls below a predetermined threshold. In this regard, charge module 1112 may provide additional energy to allow for longer training or running sessions of individual 500.

In some embodiments, software platform 1000 includes a Guide module 1114. Guide module 1114 may utilize audio system 116, for example, to serve as a guide for a blind individual 500. In some embodiments, guide module 1114 may travel ahead of individual 500 and "scout" the area, for example. In some embodiments, guide module 1114 may include a light, for example, an LED light that may be configured to turn on if the environment sensed by sensor module 102 drops below a predetermined light level threshold.

In some embodiments, software platform 1000 includes a Babysitter module 1116. Babysitter module 1116 may configure robotic platform such that it autonomously "walks" an individual's 500 baby around a predetermined path (e.g., around the block). In some embodiments, babysitter module may "walk" an individual's canine companion. In some embodiments, babysitter module 1116 may stream video data from video camera 114 to electronic device 400 for monitoring by individual 500.

In some embodiments, software platform 1000 includes a light module 1118 that may activate a light on robotic platform 100 to illuminate a path for individual to follow.

In some embodiments, software platform 100 includes vision module 1120. Vision module 1120 may, for example, utilize video camera 114, or sensor array 108, or additional sensors to achieve computer vision for system 10. In some embodiments, vision module 1120 may be a sub-module of other modules.

In some embodiments, software platform 1000 may include a Fetch module 1124. Fetch module 1124 may communicate with sensor module 102, and be configured to find and retrieve athletic equipment, for example, soccer balls, or golf balls.

In some embodiments, software platform 1000 includes a weather module 1126. Weather module 1126 may communicate with sensor module 102, for example, and record/ report wind speed, temperature, humidity, etc. This data may be fed back into other modules, for example, to adjust workouts of individual based on weather information.

In some embodiments, software platform 1000 includes referee module 1128. Referee module 1128 may communicate with athletic equipment, for example soccer balls and the like. In some embodiments sensor module 102 may determine whether a soccer ball is out of bounds for example, or travels past a goal line.

In some embodiments, software platform 1000 includes skills module 1130. Skills module 1130 may configure robotic platform 100 to perform athletic maneuvers, for example, "kicking" soccer balls for goalie/player training. In some embodiments, robotic platform 100 may be configured to travel in random or pseudorandom patterns, and have individual 500 follow it. Skills module 1130 may include a simulated race mode, such that individual 500 may attempt to follow the robotic platform 100 as it leads them through a simulated race. In some embodiments, skills module 1130 may include a World Record mode. In the world record mode, the robotic platform 100 may lead individual 500 at a world record pace for a particular distance. In some embodiments, world record mode may configure robotic platform 100 to "replay" world record or personal record performances so the runner can attempt to "hang on" as long as possible. For example, drive system 104 may accelerate and decelerate at a specific pace, e.g., the acceleration at the start and the "kick" at the end of the race, for example.

In some embodiments, software platform 100 includes team module 1132. Team module 1132 may provide feedback to multiple individuals 500, or coordinate movement between In some embodiments, software platform 1000 includes a social module 1134, for example, to integrate with social networking platforms, or other communication systems such that an individual may stream video of their workout. For example, social module 1134 may enable individual 500 to video chat with other individuals engaged in a workout. In some embodiments, social module 1134 may allow for friends, family, or fans of an individual engaged in a workout to communicate with the individual, for example to cheer them on (e.g., transmit a song designed to encourage or "pump up" individual 500, or phone a friend when individual 500 is fatigued). In some embodiments, social module 1134 may include communicating to a communication hub for services, (e.g., such as "OnStar").

In some embodiments, the individual 500 may use robotic training system 10 to carry out the methods and systems of the present invention. In some embodiments, the individual 500 may use an electronic device 400 to carry out the methods and systems of the present invention.

After launching the application software (e.g., software platform 1000), the individual 500 may cause different GUI pages to be provided by different modules by selecting their corresponding icons using user input controls. Additional icons corresponding to sub-modules or program wizards associated with a particular module may pop up or otherwise be displayed to the individual 500 if the individual 500 selects, swipes, or hovers over a module icon with a cursor.

In some embodiments there may be an educational section. In some embodiments this may include information general to health and fitness, or more specialized information, such as information about running or a particular athletic activity.

In some embodiments, the system may archive individual 500 information in an acceptable way to allow for more storage room on the electronic device 400 or sensor module 104. Archival may include hard drive storage on site, cloud based storage, server storage, or any other acceptable storage medium.

Examples of athletic goals may include training for a race, or other sporting event, improving individual fitness, simply enjoy running, or the like. Frequency intervals may include for example about 1-2 times per week, about 3-4 times per week, about 5-7 times per week, or the individual doesn't know. Length intervals may include for example about less than about 5 miles per week, about 5-10 miles per week, about 10-20 miles per week, greater than about 20 miles per week, or the individual doesn't know. Examples of intended athletic terrain environments may include roads, track, treadmill, trail, gym, or particular athletic fields designed for a specific sport. These features may be integrated into software platform 1000 and used to control robotic training system 10.

All modules may have one or more sub-modules which may be navigated to and from by clicking, swiping, etc. In some embodiments, the system may allow the individual 500 one of upload photos, videos, medical records, and the like for incorporation into the robotic training system and methods.

Pairing is a process used in computer networking that helps set up an initial linkage between computing devices to allow communications between them. Pairing may occur wirelessly via a personal area network or local area network using, for example, the Bluetooth wireless protocols. The software platform 1000 may prompt the individual 500 to pair their electronic device 400 (or other sensors) to a sensor module 102, and may display updates to the individual 500 as to the status of the pairing.

Sensor modules 102 may have a generic registration name in the system that identifies the sensor module as part of the system 10. Once paired, sensor modules may be identified by the name of the individual using that sensor module. For example a sensor might be registered as RSS0005 as a generic identification name, and the broadcast signal would include this name. Once paired that sensor module may change the broadcast signal to include a name corresponding to the particular individual using that sensor module, such as NAME01 or NAME02. Once the sensor modules 102 are paired, registration data and personal information collected from the individual 500 may be loaded onto the sensor modules.

In some embodiments, the system 10 or method may include identifying whether a performance goal has been met. In some embodiments, the method may include receiving personal information about the individual prior to receiving the data about the individual. The personal information may include information such as their name, prior injury information, height, weight, gender, shoe size, an athletic goal, intended athletic environment or terrain, intended athletic activity duration, intended athletic activity frequency, intended athletic activity distance, quantitative or qualitative preferences about athletic equipment or footwear (such as level of cushion, preference of weight, materials and the like), and current athletic footwear.

In other embodiments, the method may include creating an account for the individual. This account may include obtaining personal information from the individual. The method may include receiving motion data related to the individual from a sensor module associated with the individual while the individual is engaged in an athletic activity, or other data received from robotic platform 100 and associated sensor modules 102. In some embodiments, the method may include storing the personal information, and characteristics in association with the account for the individual.

In some embodiments, the electronic device 400 may be for example one of a desktop computer, a PDA device, MP3 player, an electronic watch having a sports operating mode, a workstation, mobile device (e.g., a mobile phone, personal digital assistant, tablet computer, or laptop), computer, server, compute cluster, server farm, game console, set-top box, kiosk, embedded system, a gym machine, dedicated electronic device, game console controller. In some embodiments, electronic device 400 may include at least one processor and memory.

Robotic training system 10 according to embodiments of the present invention may be suitable for use by individuals 400 for individual athletic activities may be suitable for use by individuals 400 engaged in athletic activities such running or walking.

In some embodiments of the present invention, the robotic training system 10 may also include or interact with robotic training system software platform 1000. Interface aspects of the robotic training system or robotic training system software could be, for example, presented to an individual 500 via a screen on the individual's 500 electronic device 400. In some embodiments, software platform 1000 may be remotely hosted, for example, on a server. In some embodiments, an individual may download software platform 1000 or various modules to a memory, for example, a flash drive, which may be coupled to the robotic training system 10 to program the robotic platform 100.

In some embodiments, additional sensors may be utilized, for example additional physiological sensors integrated within an existing piece of athletic activity monitoring equipment such as, for example, a heart rate monitoring device, a pedometer, and accelerometer-based monitoring device, positioning system receiver device (e.g. a GPS receiver), or other fitness monitoring device.

Communication may also occur between the sensors, electronic device, and/or a remote server 604 via a network 602, for example, as shown in FIG. 5. In some embodiments, the network is the Internet. The Internet is a worldwide collection of servers, routers, switches and transmission lines that employ the Internet Protocol (TCP/IP) to communicate data. The network may also be employed for communication between any two or more of the sensors, the electronic device, the server, etc. In some embodiments of the present invention, information is directly communicated between the sensors or processor and the server via the network, thus bypassing the electronic device.

A variety of information may be communicated between any of the components that may transmit or receive data or information. Such information may include, for example, performance parameter data, device settings (including sensor settings), software, and firmware.

Communication among the various elements of the present invention may occur after the workout/athletic activity has been completed or in substantially real-time during the workout/athletic activity.

The electronic device 400 may serve a variety of purposes including, for example, providing additional data processing, providing instructions to robotic platform 100; providing additional data storage, providing data visualization, providing additional sensor capabilities, relaying information to a network 602, providing for the playback of music or videos, or the like.

The electronic device 400 illustrated in the figures may not be a dedicated electronic monitoring device; the electronic device 400 illustrated in the figures may be a mobile phone, dedicated fitness monitor, smart watch, tablet computer, etc. In alternate embodiments, it may be possible for the sensor module 102 itself to be embodied by a mobile phone, or for the electronic device 400 to be a mobile phone. Including an electronic device 400 in the robotic training system 10, such as a mobile phone, may be desirable as mobile phones are commonly carried by individuals 400, even when engaging in athletic activities, and they are capable of providing significant additional computing and communication power at no additional cost to the individual 500.

In view of the above discussion, it is apparent that various processing steps or other calculations recited herein may be capable of being performed by various embodiments of the robotic training system 10 disclosed herein, and are not necessarily limited to being performed by the sensor module 102, depending on the configuration of a particular embodiment of the present invention. For example, any of the processing steps or other calculations recited herein may be performed, in various embodiments, by the sensor module 102, by a server computer 604, by an electronic device 400, and/or any other network component, or by more than one component.

Embodiments of the present invention may involve the use of so-called "cloud computing." Cloud computing may include the delivery of computing as a service rather than a product, whereby shared resources, software, and information are provided to computers and other devices as a utility over a network (typically the Internet). Cloud computing may entrust services (typically centralized) with an individual's 500 data, software and computation on a published application programming interface over a network. End users may access cloud-based applications through a web browser or a light weight desktop or mobile app while the business software and data are stored on servers at a remote location. Cloud application providers often strive to give the same or better service and performance than if the software programs were installed locally on end-user computers.

Embodiments of the present invention may incorporate features of motion and performance monitoring systems. Exemplary motion monitoring and performance systems are disclosed in commonly owned U.S. patent application Ser. No. 13/077,494, filed Mar. 31, 2011 (which published as U.S. Patent App. Pub. No. 2012/0254934), and commonly owned U.S. patent application Ser. No. 13/797,361, filed Mar. 12, 2013 (which published as U.S. Patent App. Pub. No. 2014/0266160), the entirety of each being incorporated herein by reference thereto.

An overview of exemplary embodiments of components of the robotic training system 10 of the present invention, including exemplary sensor modules 102, has been provided above.

Figure 7:
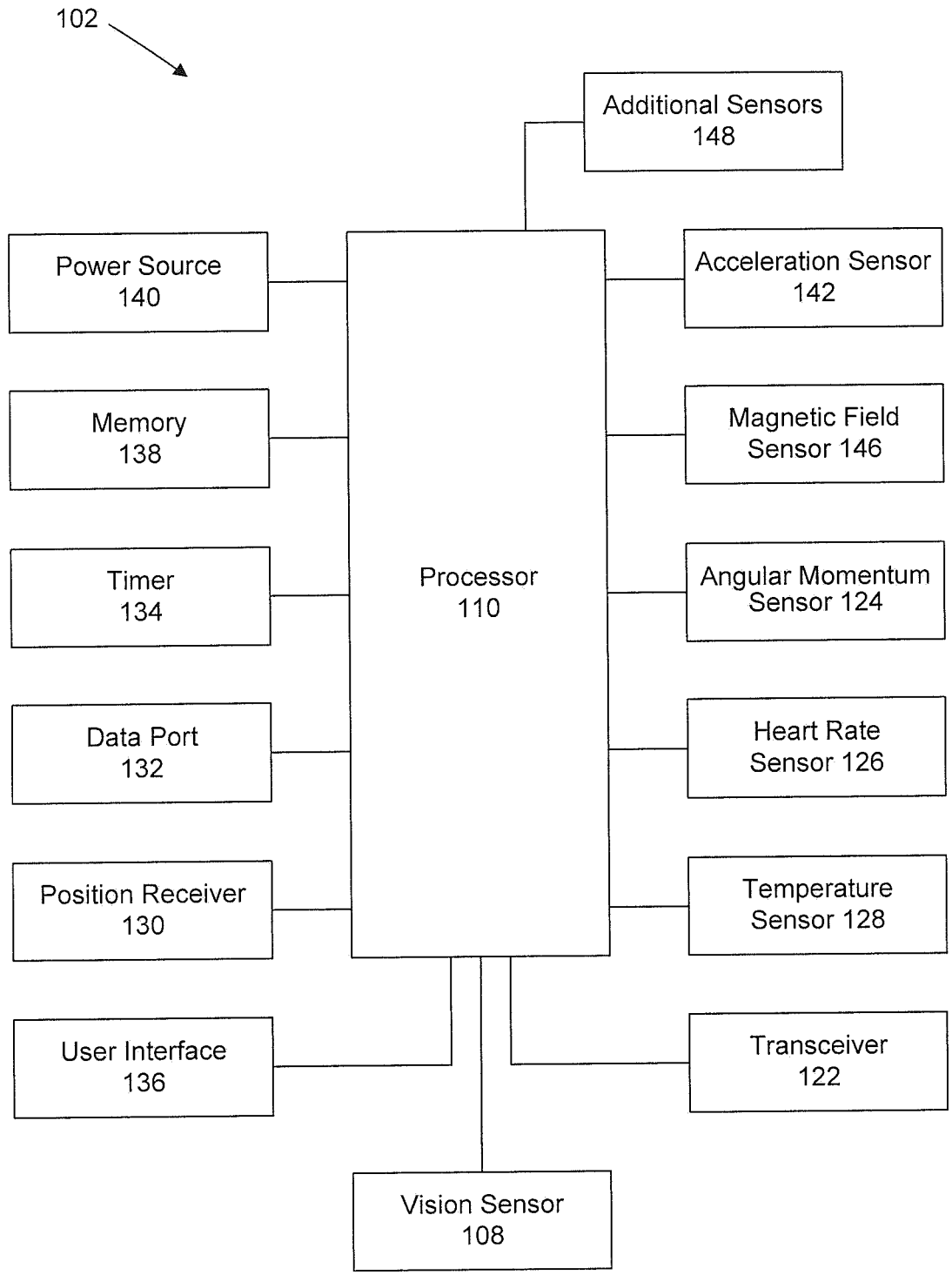
FIG. 7 is a diagram of a sensor module according to an embodiment of the present invention.

Turning to FIG. 7, a block diagram of components of a sensor module 102 according to some embodiments of the present invention is shown. In the illustrated embodiment, the sensor module 102 may include processor 110 (processor 110 may also be a separate component). Sensor module 102 may include a power source 140, a memory 138, an acceleration sensor 142, a magnetic field sensor 146, and a transceiver 112 (transceiver 112 may be a separate component). These components are operatively connected to one another to carry out the functionality of the sensor module 102. In other embodiments, one or more of these sensor module 102 components may be omitted, or one or more additional components may be added. Processor 110 may be included in sensor module 102, or may be a separate component. Processor 110 may be adapted to implement application programs stored in the memory 138 of the sensor module 102. The processor 110 may also be capable of implementing analog or digital signal processing algorithms such as raw data reduction and filtering. For example, processor 110 may be configured to receive raw data from sensors and process such data at the sensor module 102. The processor 110 is operatively connected to the power source 140, the memory 138, the acceleration sensor 142, the magnetic field sensor 146, and the transceiver 112.

In an embodiment, calibration of sensor module 102 is performed using, for example, received GPS signals from a position receiver 130. The received GPS signals can be used, for example, to determine a distance that an individual runs or walks during a workout. In other embodiments, calibration of sensor module 102 may be prepared by using a counter (e.g., additional sensor 148) to count revolutions of an axle of drive system 104, for example.

The power source 140 may be adapted to provide power to the sensor module 102. In one embodiment, the power source 140 may be a battery. The power source may be built into the sensor module 102 or removable from the sensor module 102, and may be rechargeable or non-rechargeable. In some embodiments, the power source 140 may be recharged by a cable attached to a charging source, such as a universal serial bus ("USB") FireWire, Ethernet, Thunderbolt, or headphone cable, attached to a personal computer. In another embodiment, the power source 140 may be recharged by inductive charging, wherein an electromagnetic field is used to transfer energy from an inductive charger to the power source 140 when the two are brought in close proximity, but need not be plugged into one another via a cable. In some embodiment, a docking station may be used to facilitate charging. In other embodiments, the sensor module 102 may be repowered by replacing one power source 140 with another power source 140. Power source 140 may additionally power robotic platform 100, including drive and steering systems 104/106.

The memory 138 may be adapted to store application program instructions and to store athletic activity data. In some embodiments, the memory 138 may store application programs used to implement aspects of the functionality of the retail enhancement system 10 described herein. In one embodiment, the memory 138 may store raw data, recorded data, and/or calculated data. In some embodiments, as explained in further detail below, the memory 138 may act as a data storage buffer. The memory 138 may include both read only memory and random access memory, and may further include memory cards or other removable storage devices.

In some embodiments of the present invention, the memory 138 may store raw data, recorded data, and/or calculated data permanently, while in other embodiments the memory 138 may only store all or some data temporarily, such as in a buffer. In one embodiment of the present invention, the memory 138, and/or a buffer related thereto, may store data in memory locations of predetermined size such that only a certain quantity of data may be saved for a particular application of the present invention.

The acceleration sensor 116 may be adapted to measure the acceleration of the sensor module 102. Accordingly, when the sensor module 102 is physically coupled to robotic platform 100, the acceleration sensor 116 may be capable of measuring the acceleration of the object 100, including the acceleration due to the earth's gravitational field, and may allow robotic platform to move with predetermined acceleration patterns. In one embodiment, the acceleration sensor 116 may include a tri-axial accelerometer that is capable of measuring acceleration in three orthogonal directions. In other embodiments one, two, three, or more separate accelerometers may be used.

The magnetic field sensor 146 may be adapted to measure the strength and direction of magnetic fields in the vicinity of the sensor module 102. Accordingly, sensor module 102, utilizing the magnetic field sensor 146, may be capable of measuring the strength and direction of magnetic fields in the vicinity of the robotic platform 100, including the earth's magnetic field. In one embodiment, the magnetic field sensor 146 may be a vector magnetometer. In other embodiments, the magnetic field sensor 146 may be a tri-axial magnetometer that is capable of measuring the magnitude and direction of a resultant magnetic vector for the total local magnetic field in three dimensions. In other embodiments one, two, three, or more separate magnetometers may be used.

In one embodiment of the present invention, the acceleration sensor 116 and the magnetic field sensor 146 may be contained within a single accelerometer-magnetometer module bearing model number LSM303DLHC made by STMicroelectronics of Geneva, Switzerland. In other embodiments, the sensor module 102 may include only one of the acceleration sensor 116 and the magnetic field sensor 146, and may omit the other if desired.

The transceiver 122 depicted in FIG. 6 may enable the sensor module 102 to wirelessly communicate with other components of the robotic training system 10, such as those described in further detail below. In one embodiment, the sensor module 102 and the other local components of the robotic training system 10 may communicate over a personal area network or local area network using, for example, one or more of the following protocols: ANT, ANT+ by Dynastream Innovations, Bluetooth, Bluetooth Low Energy Technology, BlueRobin, or suitable wireless personal or local area network protocols. Other known communication protocols suitable for a robotic training system 10 may also be used.

In one embodiment, the transceiver 122 is a low-power transceiver. In some embodiments, the transceiver 122 may be a two-way communication transceiver 122, while in other embodiments the transceiver 122 may be a one-way transmitter or a one-way receiver. Wireless communication between the sensor module 102 and other components of the robotic training system 10 is described in further detail below. In other embodiments, the sensor module 102 may be in wired communication with other components of the robotic training system 10 that does not rely on transceiver 122.

In some embodiments of the present invention, a sensor module 102 having components such as those depicted in FIG. 6 may be physically coupled to robotic platform 100 during an athletic activity conducted by an individual 500. Sensor module 102 may further monitor changes in the spatial orientation of the individual's 500 body or a piece of the individual's athletic equipment or article of footwear, or to determine a correlation between body or equipment movement data and a characteristic such as gait characteristic. In some embodiments, sensor module 102, as described, may be used to monitor the surface of a track, for example, to follow chalk/paint line 302. In some embodiments, additional sensors not coupled to robotic platform 100 (e.g., other acceleration sensors, physiological sensors, etc.) may be responsible for collecting the data necessary to carry out the various monitoring calculations.

In some other embodiments, however, it may be desirable to have additional sensors 148 (for example, such as speed sensors, etc.) included within the sensor module 102, or operatively connected to sensor module 102, or to have additional sensors in communication with the sensor module 102. In some embodiments, an additional sensor module 102 may be integrated within an existing piece of athletic activity monitoring equipment possibly having additional or different sensors such as, for example, a heart rate monitoring device, a pedometer, and accelerometer-based monitoring device, or other fitness monitoring device.

In addition to the acceleration sensor 116 and the magnetic field sensor 146, other sensors that may be part of the sensor module 102 or separate from but in communication with the sensor module 102 may include sensors capable of measuring a variety of athletic performance parameters. The term "performance parameters" may include physical parameters and/or physiological parameters associated with the individual's 500 athletic activity. Physical parameters measured may include, but are not limited to, time, distance, speed, pace, pedal count, wheel rotation count, rotation generally, stride count, stride length, airtime, stride rate, altitude, strain, impact force, jump force, force generally, and jump height. Physiological parameters measured may include, but are not limited to, heart rate, respiration rate, blood oxygen level, blood lactate level, blood flow, hydration level, calories burned, or body temperature.

As shown in FIG. 7, in some embodiments, sensor module 102 may incorporate other additional components. In some embodiments, sensor module 102 may incorporate an angular momentum sensor 124, a heart rate sensor 126, a temperature sensor 128, a position receiver 130, a data port 132, and a timer 134 operatively connected to one another to carry out the functionality of the sensor module 102. In other embodiments, one or more of these sensor module 102 components may be omitted, or one or more additional components may be added.

In some embodiments, the transceiver 122 may be a two-way communication transceiver 122, while in other embodiments the transceiver 122 may be a one-way transmitter or a one-way receiver.

The user interface 136 of the sensor module 102 may be used by the individual 500 to interact with the sensor module 102. In some embodiments, the user interface 136 may include one or more input buttons, switches, or keys, including virtual buttons, switches, or keys of a graphical user interface touch screen surface. The function of each of these buttons, switches, or keys may be determined based on an operating mode of the sensor module 102. In one embodiment, the user interface 136 may include a touch pad, scroll pad and/or touch screen. In another embodiment, the user interface 136 may include capacitance switches. In a further embodiment, the user interface 136 may include voice-activated controls.

In some embodiments, however, the sensor module 102 may not include a user interface 136. In these embodiments, the sensor module 102 may be capable of communicating with other components of the robotic training system 10 which may themselves include user interfaces, for example, electronic device 400.

The angular momentum sensor 124, which may be, for example, a gyroscope, may be adapted to measure the angular momentum or orientation of the sensor module 102. Accordingly, when the sensor module 102 is physically coupled to robotic platform 100, the angular momentum sensor 124 may be capable of measuring the angular momentum or orientation of the object 104. In one embodiment, the angular momentum sensor 124 may be a tri-axial gyroscope that is capable of measuring angular rotation about three orthogonal axes. In other embodiments one, two, three, or more separate gyroscopes may be used. In some embodiments, the angular momentum sensor 124 may be used to calibrate measurements made by one or more of the acceleration sensor 116 and the magnetic field sensor 146. This may be particularly advantageous for an aerial robotic platform 100.

The heart rate sensor 125 may be adapted to measure an individual's 500 heart rate. The heart rate sensor 125 may be placed in contact with the individual's 500 skin, such as the skin of the individual's chest, and secured with a strap. The heart rate sensor 125 may be capable of reading the electrical activity the individual's 500 heart.

The temperature sensor 128 may be, for example, a thermometer, a thermistor, or a thermocouple that measures changes in the temperature. In some embodiments, the temperature sensor 128 may primarily be used for calibration other sensors of the robotic training system 10, for example, the acceleration sensor 116 and the magnetic field sensor 146.

In one embodiment, the position receiver 130 may be an electronic satellite position receiver that is capable of determining its location (i.e., longitude, latitude, and altitude) using time signals transmitted along a line-of-sight by radio from satellite position system satellites. Known satellite position systems include the GPS system, the Galileo system, the BeiDou system, and the GLONASS system. In another embodiment, the position receiver 130 may be an antenna that is capable of communicating with local or remote base stations or radio transmission transceivers such that the location of the sensor module 102 may be determined using radio signal triangulation or other similar principles. In some embodiments, position receiver 130 data may allow the sensor module 102 to detect information that may be used to measure and/or calculate position waypoints, time, location, distance traveled, speed, pace, or altitude.

The data port 132 may facilitate information transfer to and from the sensor module 102 and may be, for example, a USB port. In some exemplary embodiments, data port 132 can additionally or alternatively facilitate power transfer to a power source, in order to a charge power source.

The timer 134 may be a clock that is capable of tracking absolute time and/or determining elapsed time. In some embodiments, the timer 134 may be used to timestamp certain data records, such that the time that certain data was measured or recorded may be determined and various timestamps of various pieces of data may be correlated with one another.

In some embodiments, the sensor module 102 may also include a button and/or a display. The button may serve as the user interface of the sensor module 102. The button may be capable of turning the sensor module 102 on and off, toggling through various display options, or serving a variety of other functions. Alternatively, multiple buttons or no buttons may be provided. In one embodiment, the display may be a relatively simple LED display that is capable of conveying the status or battery life of the sensor module 102 to an individual 500 with different color combinations or flashing patterns, for example. In another embodiment, the display may be a more advanced display that is capable of displaying performance parameter information, feedback, or other information to the individual 500, such as a segmented LCD display. Alternatively, no button or display may be provided.

In other embodiments, the sensor module 102 may include audio controls such as a speaker and/or microphone for audio communication with an individual 500. These components may serve as the user interface of the sensor module 102, and may be included in audio input system 120. These audio controls may be capable of turning the sensor module 102 on and off, toggling through various display options, or serving a variety of other functions. In one embodiment, the audio controls may be capable of conveying the status or battery life of the sensor module 102 to an individual 500. In another embodiment, the audio controls may be capable of outputting or receiving performance parameter information, feedback, or other information to and from the individual 500. In one embodiment, the audio controls may be capable of accepting voice commands form the individual 500. In another embodiment, the sensor module 102 may be capable of relaying audio information to an individual wirelessly via another device, such as a pair of headphones. Alternatively, audio controls may be provided.

Data obtained by the sensor module 102 may be processed in a variety of ways to yield useful information about the motion of an object 104 of interest during the activity. In some embodiments, sensor module 102 data may be processed to monitor changes in the spatial orientation of the individual's 500 body or a piece of the individual's 500 athletic equipment. In other embodiment, sensor module 102 data may be processed to by reference to a predetermined correlation between movement data and a characteristic stored in a data structure.

In some embodiments, sensor modules 102 are used to detect changes in an individual's direction of motion. Sensor modules 102 according to the present invention can also be worn by individuals and used to detect and/or track other motions such as, for example, motions associated with push-ups, pull-ups, weightlifting, diving, gymnastics, et cetera.

Figure 8:
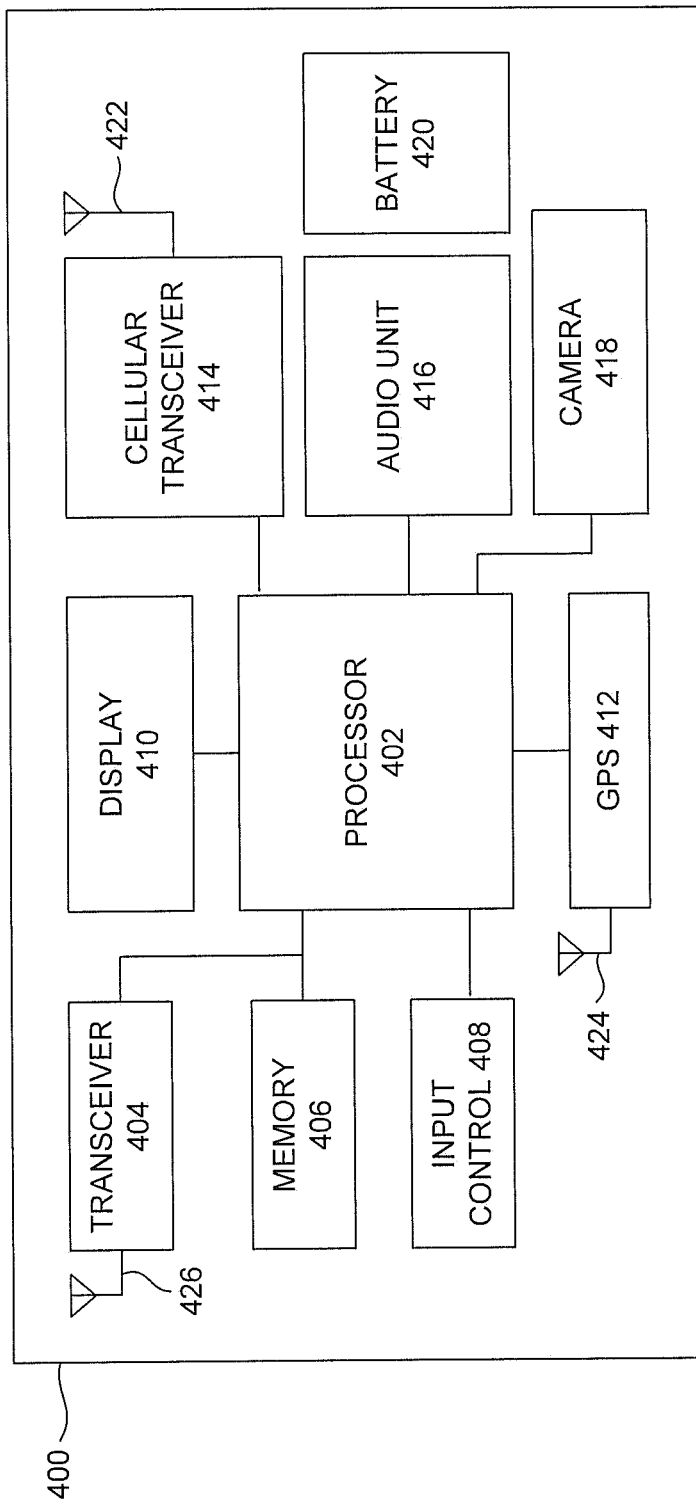
FIG. 8 is a diagram of an electronic device according to an embodiment of the present invention.

Turning to FIG. 8, a block diagram of electronic device 400 according to an embodiment of the present invention is shown. In an embodiment, electronic device 400 corresponds to a mobile computing device, mobile phone, desktop computer, tablet computer, dedicated electronic device, or the like. As shown in FIG. 7, electronic device 400 may include a processor 402, memory 406, a user input control 408, a display 410, an audio unit 416, a transceiver 404, a cellular transceiver 414, an optional satellite-based positioning system receiver 412, a camera 418, and a battery 420.

Processor 402 is a processor capable of implementing application programs or software platforms 1000 stored in memory 406. Processor 402 is also capable of implementing digital signal processing algorithms. Processor 402 is coupled to memory 304, user input control 408, display 410, audio unit 416, transceiver 404, and may include a cellular transceiver 414.

Memory 406 is used to store application program instructions (e.g., software platform 1000) and data. In an embodiment, memory 406 stores programs, for example, used to implement all of the functionality of a typical electronic device. In an embodiment, memory 406 includes both read only memory and random access memory.

User input control 408 is used by an individual to interact with electronic device 400. In an embodiment, user input control 408 includes a variety of input buttons and/or keys. The function of each of these buttons and/or keys is typically determined based on an operating mode of electronic device 400. In one embodiment, user input control 408 includes a touch pad or scroll pad and/or touch screen buttons.

Display 410 is used to display information to an individual. In an embodiment, display 410 is a liquid crystal display.

Camera 418 is a small digital camera used to take digital photos or video. In one embodiment, camera 418 is a CCD camera. In another embodiment, camera 418 is a CMOS camera.

Audio unit 416 is used to process audio signals. In an embodiment, voice signals picked up using a microphone are converted to digital signals so that they can be operated upon, for example, by processor 402. Audio unit 416 also converts, for example, digital audio signals into amplified analog audio signals that can be used to drive one or more speakers. In an embodiment, audio unit 416 implements signal processing algorithms such as those available from Dolby Laboratories, Inc., which enhance the quality of music.

Transceiver 404 is a low-power transceiver used to communicate with other components of robotic training system 10. In an embodiment, transceiver 404 operates in an unlicensed frequency band such as 2.4 GHz. Transceiver 404 is coupled to an antenna 314. As used herein, the term transceiver means a combination of a transmitter and a receiver. In an embodiment, the transmitter and the receiver are integrated and form, for example, a part of an intergraded circuit.

Cellular transceiver 414 may be used to send and receive, for example, voice cellular telephone signals. Transceiver 414 can also be used to exchange information with a computer network such as, for example, the Internet. Cellular transceiver 414 is coupled to an antenna 422. As used herein, the term cellular transceiver means a combination of a cellular transmitter and a cellular receiver. In an embodiment, the transmitter and the receiver are integrated together into a single device.

In one embodiment, cellular transceiver 414 is used to send data described herein to a location where it is analyzed, for example, by a professional trainer. The professional trainer can call or text message the individual and provide the individual substantially real-time feedback based on the data. If the individual wants to call the professional trainer, for example, during a workout, the individual can place a call to the professional trainer, for example, by tapping electronic device 400 to place a call to a stored telephone number. In one embodiment, tapping electronic device 400 sends a text message to the professional trainer requesting that the professional trainer call the individual. These functions may also be included in sensor module 102.

Battery 420 is used to provide power to operate the various components of electronic device 400. In an embodiment, battery 420 is recharged periodically using a power adapter that plugs into a typical household power outlet. Battery 420 can also be a non-rechargeable battery.

In an embodiment, electronic device 400 also includes an optional satellite-based positioning system (e.g., global positioning system (GPS) or Galileo system) receiver 412. This enables the electronic device to determine its location anywhere on the earth. The satellite-based positioning system (e.g., GPS) receiver 412 is coupled to an antenna 424. In an embodiment, GPS receiver 412 enables the electronic device 400, for example, to provide navigational instructions to a runner using the device. The directions for a running route can be downloaded to the electronic device prior to a run and stored in memory 406. In addition to navigational instructions, attributes about the running route such as, for example, whether the route has sidewalks, is on a trail, is located within a safe neighborhood, et cetera, can also be downloaded and viewed. GPS receiver 412 can be used, in an embodiment, to track a route run by a runner. The route can be saved in memory 304 and viewed by the runner after the run. The route can also be shared with other runners, for example, by posting the route on a computer/web server for down-loading by other runners.

In an embodiment, GPS receiver 412 and information stored in the memory of electronic device 400 (or information received, e.g., from the internet using cellular transceiver 414) are used to provide navigational instructions, for example, to a runner. In an embodiment, the runner can enter into electronic device 400 that he or she would like to run five kilometers, for example, and the electronic device will automatically select/map-out an appropriate route and provide navigation instructions to the runner during the run. In an embodiment, the runner can specify both a start point and a stop point for the run. In an embodiment, only one point is specified, which serves as both the start point and the stop point. In an embodiment, the start and stop points are the point at which the runner is standing (e.g., as determined by GPS receiver 412) when the runner enters, for example, that he or she would like to run five kilometers.

In an embodiment, electronic device 400 includes a radio. The radio can be an AM only radio, an FM only radio, or both an AM and FM radio. In an embodiment, the radio is controlled using soft keys presented to an individual on display 410.

In one embodiment, electronic device 400 includes optional sensors (not shown) for detecting selected weather related data such as, for example, temperature, humidity, ultra-violet radiation and/or barometric pressure. This data can be used, for example, to determine how an individual's performance is effected by environmental factors.

In one embodiment, an electronic device according to the present invention does not include a display. In this embodiment, information such as, for example, performance and/or feedback information is provided to an individual audibly during a workout, e.g., through sensor module 102, or other audio feedback. The information can be display to the individual, for example, after the workout using a computer display once the information has been transferred to the computer. In an embodiment, the information can be transferred to a second processing device such as, for example, a sports watch during the workout and displayed to the individual during the workout on the display of the second processing device.

In embodiments, an electronic device 400 according to the present invention can be formed, for example, by attaching a dongle (e.g., a small hardware device that protects software) to a conventional phone, a music file player, a personal digital assistant, et cetera. The dongle includes, for example, downloadable software that implements some or all of the sport functions described herein. In an embodiment, the software includes a sport user interface written in the Java programming language. In an embodiment, the software includes drivers, for example, that enable the software to be used with any ultra low power Bluetooth communications protocol compatible device. Other embodiments are compatible with other communications protocol compatible devices.

In an embodiment of the present invention, a electronic device according to the present invention is a dedicated device (rather than a device such as, for example, a phone, a music file player, or a personal digital assistant) that implements the robotic training functions as detailed herein.

In some embodiments, the sensor module 102 may then determine that the movement of an individual 500 indicates the occurrence of a movement to track. In one embodiment, the determination that the movement of the individual 500 indicates the occurrence of a movement to track occurs when a threshold data value is met for a predetermined period of time. For example, the sensor module 102 may determine that a movement of the individual has resulted in a threshold acceleration occurring for a predetermined period of time. This may initiate movement of the robotic platform 100.

In some embodiments, remote processing may be used to augment the processing discussed herein. The remote processing may enable a sensor module 102 to wirelessly transmit data to a remote computer for processing. Wireless communication with other elements of the robotic training system 10 is generally described above. In this way, the processing capabilities of the robotic training system 10 may be enhanced by shifting certain processing and analytical tasks to a remotely located computer, such as a server computer, with greater computational abilities and, in some embodiments, access to additional data or other resources.

In some embodiments, the data received may be transmitted to the remote computer during the athletic activity. In another embodiment, the data received may be transmitted to the remote computer after the athletic activity has been completed.

In some embodiments, the physiological data received may be compared to data associated with the individual 500 for the present athletic activity and data associated with the individual 500 from a previous athletic activity. In some embodiments, the data may be compared to data received during a different individual's 500 athletic activity.

By using the robotic training system 10 including the sensor module 102 described above, embodiments of the present invention may advantageously enable the individual 500 (or their coach, teammate, a spectator, friends, competitors, etc.) to obtain this or other information about the motion of the individual's 500 body or the motion of a piece of the individual's 500 athletic equipment during or after the course of the athletic activity.

While various embodiments of the present invention are described in the context of the running, the present invention is not so limited and may be applied in a variety of different sports or athletic activities including, for example, sports of soccer (i.e., football), basketball baseball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto.

For running, sensor module 102 embodiments such as those described above may enable an individual 500, to determine, for example, characteristics of a runner's motion. For example, a sensor module 102 could be used to determine the speed, pace, distance traversed, locations traversed, or to discriminate between different surfaces (e.g., grass, street, or trail) and inclinations (e.g., uphill, flat, or downhill). In some embodiments the sensor module 102 may be mounted, for example, on a runner's torso, arm, hand, leg, foot, or head, or on or in their article of footwear, or integrated into robotic platform 100

In some embodiments of the present invention, the sensor module 102 may be capable of compensating for inherent deficiencies that may be present for various types of sensor contained within or in communication with the sensor module 102. Most real world sensors have limitations. For example, accelerometers, magnetometers, and gyroscopes may have accuracy issues, particularly when used at speeds of motion of the object 104 or under other conditions that differ from their initial calibration conditions.

In some embodiments of the present invention, the sensor module 102 may communicate with other components of the robotic training system 10 via wired or wireless technologies. Communication between the sensor module 102 and other components of the robotic training system 10 may be desirable for a variety of reasons. For example, to the extent that the sensor module 102 records and stores athletic activity information, it may be useful to transmit this information to another electronic device for additional data processing, data visualization, sharing with others, comparison to previously recorded athletic activity information, or a variety of other purposes. As a further example, to the extent that the sensor module 102 has insufficient processing power, wide area network transmission capabilities, sensor capabilities, or other capabilities, these capabilities can be provided by other components of the robotic training system 10. With this in mind, possible communications means are described briefly below.

Wired communication between the sensor module 102 and an electronic device 400 may be achieved, for example, by placing the sensor module 102—or a piece of athletic equipment 104 including the sensor module 102—in a docking unit that is attached to the electronic device 400 using a communications wire plugged into a communications port of the electronic device 400. In another embodiment, wired communication between the sensor module 102 and the electronic device 400 may be achieved, for example, by connecting a cable between the sensor module 102—or a piece of athletic equipment including the sensor module 102—and the computer or standalone device 600. The data port 132 of the sensor module 102 and a communications port of the computer 600 may include USB ports. The cable connecting the sensor module 102 and the computer 600 may be a USB cable with suitable USB plugs including, but not limited to, USB-A or USB-B regular, mini, or micro plugs, or other suitable cable such as, for example, a FireWire, Ethernet or Thunderbolt cable. As previously explained above, in some embodiments, such cables could be used to facilitate power transfer to a power source of the sensor module 102, in order to charge the power source. Alternatively, the power source may be recharged by inductive charging, or by using a docking station with a charging base.

Wired connection to an electronic device 400 may be useful, for example, to upload athletic activity information from the sensor module 102 to the electronic device 400, or to download application software updates or settings from the electronic device 400 to the sensor module 102.

Wireless communication between the sensor module 102—or a piece of athletic equipment including the sensor module 102—and the electronic device 400 may be achieved, for example, by way of a wireless wide area network (such as, for example, the Internet), a wireless local area network, or a wireless personal area network. As is well known to those skilled in the art, there are a number of known standard and proprietary protocols that are suitable for implementing wireless area networks (e.g., TCP/IP, IEEE 802.16, Bluetooth, Bluetooth low energy, ANT, ANT+ by Dynastream Innovations, or BlueRobin). Accordingly, embodiments of the present invention are not limited to using any particular protocol to communicate between the sensor module 102 and the various elements of the retail enhancement system 10 of the present invention.

In one embodiment, the sensor module 102—or a piece of athletic equipment including the sensor module 102 may communicate with a wireless wide area network communications system such as that employed by mobile telephones. For example, a wireless wide area network communication system may include a plurality of geographically distributed communication towers and base station systems. Communication towers may include one or more antennae supporting long-range two-way radio frequency communication wireless devices, such as sensor module 102. The radio frequency communication between antennae and the sensor module 102 may utilize radio frequency signals conforming to any known or future developed wireless protocol, for example, CDMA, GSM, EDGE, 3G, 4G, IEEE 802.x (e.g., IEEE 802.16 (WiMAX)), etc. The information transmitted over-the-air by the base station systems and the cellular communication towers to the sensor module 102 may be further transmitted to or received from one or more additional circuit-switched or packet-switched communication networks, including, for example, the Internet.

As previously noted, in some embodiments of the present invention, sensor module 102 may communicate with an electronic device, such as a smart phone, that is also carried by the individual 500 during the athletic activity.

In some embodiments of the present invention, for example, as shown in FIG. 7, the electronic device 400 may take the form of a mobile phone and may include at least a processor, a memory, user input controls, a positioning system receiver, a wireless wide area network (WWAN) transceiver, a visual display, and an audio unit. A visual display in the form of a LCD screen, and user input controls in the form of a physical keyboard and a scroll ball may be present.

The memory of the electronic device 400 may be adapted to store application programs, software platforms or modules, used to implement aspects of the functionality of the robotic training system 10 described herein. Alternatively, those of skill in the art will understand that all or part of the software may be stored on the server 604 and accessed over the network 602 and run remotely as a mobile web application, or stored locally in robotic platform 100, having a memory.

As discussed, robotic training system 10 may include a number of different software modules capable of providing training support or other robotic platform 100 interaction to individuals 500. Each module may support one or more graphical user interfaces ("GUIs") capable of being presented to an individual 500 using the system 10.

A GUI may offer, for example, graphical elements, visual indicators, and/or text to represent information and actions available to the individual 500. The individual 500 may use a physical input device, such as keyboard or scroll ball to interact with the GUI of the system 10, for example, on electronic device 400. Alternatively, the individual 500 may use a touch screen to interact directly with what is displayed. Various touch screens such as, for example, resistive or capacitive touch screens, may be employed.

Those skilled in the art will appreciate that alternative or additional software modules and sub-modules may be implemented in order to provide or extend the described or additional functionalities to the individual 500 using the electronic device 400. For example, the software configuration of software stored on an electronic device 400 may include a device operating system, which may be one of the commercially available mobile phone operating systems such as, for example, BlackBerry OS, iPhone OS, Windows Mobile, Symbian, LINUX, WebOS, or Android. The device operating system may also have an associated application programming interface through which middleware and application programs may access the services of the operating system.

The various modules of the system 10 of the present invention may support GUIs through which an individual 500 can interact with the system 10 using the electronic device 400 just prior to and/or during an activity. As will be appreciated by those of skill in the art, in one embodiment the GUIs may be supported by a mobile device application being run on the electronic device 400. In another embodiment, the GUIs may appear as web pages provided by the server 604 via a website that may be accessible to the individual 500 over the network 602 using a web browser on their electronic device 400. The GUIs may be considered to be part of the methods or systems of the present invention.

In some embodiments, the robotic training system 10 may be sold as a package, including a robotic platform 100, an electronic device 400, sensor modules 102 for multiple individuals 500 (e.g. runners), and a charger.

Robotic training system 10 may recognize and record repeat usage of the robotic training system 10 over time, number of times various individuals store their data into a profile and update that data. The robotic training system 10 may also be able to integrate with various social media platforms, allowing individuals to share with their social network data regarding their gait characteristics, their usage of the robotic training system 10.

Various aspects of the present invention, or any parts or functions thereof, may be implemented using hardware, software, firmware, tangible non-transitory computer readable or computer usable storage media having instructions stored thereon, or a combination thereof and may be implemented in one or more computer systems or other processing systems.

As discussed, program products, methods, and systems for providing robotic training services of the present invention can include any software application executed by one or more electronic devices 400. An electronic device 400 can be any type of computing device having one or more processors. For example, the electronic device 400 can be a workstation, mobile device (e.g., a mobile phone, personal digital assistant, tablet computer, or laptop), computer, server, compute cluster, server farm, game console, set-top box, kiosk, embedded system, a gym machine, a retail system or retail enhancement system or other device having at least one processor and memory. Embodiments of the present invention may be software executed by a processor, firmware, hardware or any combination thereof in a computing device.

In this document, terms such as "computer program medium" and "computer-usable medium" may be used to generally refer to media such as a removable storage unit or a hard disk installed in hard disk drive. Computer program medium and computer-usable medium may also refer to memories, such as a main memory or a secondary memory, which can be memory semiconductors (e.g., DRAMs, etc.). These computer program products provide software to computer systems of the present invention.

Software platform may include or accept computer programs (also called computer control logic, programming data, etc.), which may be stored on main memory and/or secondary memory. Computer programs may also be received via a communications interface. Such computer programs, when executed, may enable computer systems of the present invention to implement embodiments described herein. Where embodiments are implemented using software, the software can be stored on a computer program product and loaded into a computer system using, for example, a removable storage drive, an interface, a hard drive, and/or communications interface.

Based on the description herein, a person skilled in the relevant art will recognize that the computer programs, when executed, can enable one or more processors to implement processes described above, such as the steps in the methods illustrated by the figures. In some embodiments, the one or more processors can be part of a computing device incorporated in a clustered computing environment or server farm. Further, in some embodiments, the computing process performed by the clustered computing environment may be carried out across multiple processors located at the same or different locations.

Software of the present invention may be stored on any computer-usable medium. Such software, when executed in one or more data processing device, causes the data processing device to operate as described herein. Embodiments of the invention employ any computer-usable or -readable medium, known now or in the future. Examples of computer-usable mediums include, but are not limited to, primary storage devices (e.g., any type of random access or read only memory), secondary storage devices (e.g., hard drives, floppy disks, CD ROMS, ZIP disks, tapes, magnetic storage devices, optical storage devices, MEMS, nanotechnological storage devices, memory cards or other removable storage devices, etc.), and communication mediums (e.g., wired and wireless communications networks, local area networks, wide area networks, intranets, etc.).

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments of the robotic training system described with reference to the figures will so fully reveal the general nature of the invention that others can, by applying knowledge within the skill of the art, readily modify and/or adapt for various applications such specific embodiments, without undue experimentation, without departing from the general concept of the present invention.

While various embodiments of the present invention have been described above, they have been presented by way of example only, and not limitation. It should be apparent that adaptations and modifications are intended to be within the meaning and range of equivalents of the disclosed embodiments, based on the teaching and guidance presented herein. It therefore will be apparent to one skilled in the art that various changes in form and detail can be made to the embodiments disclosed herein without departing from the spirit and scope of the present invention. The elements of the embodiments presented above are not necessarily mutually exclusive, but may be interchanged to meet various needs as would be appreciated by one of skill in the art.

It is to be understood that the phraseology or terminology used herein is for the purpose of description and not of limitation. The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

The invention claimed is:

1. A robotic athletic training system for assisting an individual during an athletic activity in an environment, comprising:
   a mobile robotic platform;
   a sensor module including an array of optical sensors coupled to the mobile robotic platform and configured to obtain sensor data from a surface of the environment over which the robotic athletic training system moves and on which the individual conducts the athletic activity;
   a drive system configured to propel the mobile robotic platform on the surface;
   a steering system configured to steer the mobile robotic platform; and
   a processor, the processor being configured to receive the sensor data from the sensor module, characterize the sensor data into at least one selected from the group of one of edge data, color data, saturation data, and threshold data, and to control at least one of the drive system and the steering system to follow a path based on the characterized data, and wherein the sensor data comprises optical data related to variation of the surface and includes data that indicates which sensor in the array of optical sensors is positioned over a line on the surface,
   wherein the system is further configured to provide coaching feedback to the individual during the athletic activity, the coaching feedback being based on the optical data.

2. The system of claim 1, wherein at least one of a speed or a direction of the mobile robotic platform is changed in response to the optical data indicating that a sensor in the sensor array has sensed the presence of a line on the surface for a predetermined time threshold.

3. The system of claim 1, further comprising:
   a wireless transceiver configured for communication with an electronic device associated with the individual,
   wherein the transceiver is configured to receive data from the electronic device and to transmit the electronic device data to the processor, and
   wherein the processor is further configured to control one of the drive system and the steering system based on the electronic device data.

4. The system of claim 3, wherein the electronic device data comprises programmed instructions to control the drive and steering systems according to a workout program.

5. The system of claim 1, wherein the path is a predetermined path.

6. The system of claim 1, further comprising:
a user interface configured to receive input data and transmit the input data received to the processor,
wherein the processor is further configured to control one of the drive system and the steering system based on the input data received from the user interface.

7. The system of claim 6, wherein the input data comprises programmed instructions to control the drive and steering systems according to a workout program.

8. The system of claim 6, wherein the user interface is integrated with the robotic training system.

9. The system of claim 1, further comprising:
a second sensor module coupled to the individual during the athletic activity,
wherein the processor is configured to receive physiological sensor data from the second sensor module.

10. The system of claim 9, wherein the physiological sensor data comprises at least one of respiratory data and cardiac data.

11. A robotic athletic training system for assisting an individual during an athletic activity in an environment, comprising:
a mobile robotic platform;
a sensor module including an array of sensors coupled to the mobile robotic platform and configured to obtain data from the environment;
a drive system configured to propel the mobile robotic platform;
a steering system configured to steer the mobile robotic platform;
a processor configured to receive data from the sensor module and to control one of the drive system and the steering system to follow a path based on the data, wherein the data comprises surface data related to variation of a surface of the environment;
a video camera configured to record video data of the individual during the athletic activity and to transmit the video data to the processor,
wherein the processor is configured to analyze a gait characteristic of the individual based on the video data, and
wherein the system is configured to provide coaching feedback to the individual during the athletic activity, the coaching feedback being based on the surface data.

12. The system of claim 11, wherein the processor is configured to analyze a physiological characteristic of the individual based on the video data, and is configured to provide coaching to the individual in response to a variation in the physiological characteristic.

13. The system of claim 11, further comprising:
an audio feedback system configured to provide information about a workout program to the individual during the athletic activity.

14. The system of claim 11, further comprising:
a display system configured to provide information about a workout program to the individual during the athletic activity.

15. The system of claim 11, further comprising:
an audio input system configured to record audio data and transmit the audio data to the processor to control the system.

16. A method of assisting an individual during an athletic activity in an environment using a robotic athletic training system, comprising:
controlling the robotic athletic training system with a processor of the robotic athletic training system to move the robotic athletic training system at a velocity;
receiving data related to a surface of the environment over which the robotic athletic training system moves and on which the individual conducts the athletic activity with a vision system of the robotic athletic training system;
comparing baseline possible surface characteristic data to the received surface data with the processor of the robotic athletic training system;
adjusting a travel direction of the robotic athletic training system in response to the comparison;
displaying information related to the athletic activity on the surface; and
providing coaching feedback to the individual during the athletic activity, the coaching feedback being based on the received surface data.

17. The method of claim 16, wherein controlling the robotic athletic training system with the processor comprises processing simulated race data such that the robotic training system moves at a predetermined race pace.

18. The method of claim 16, further comprising:
receiving physiological sensor data at the robotic athletic training system about the individual from a sensor module coupled to the individual during the athletic activity;
comparing baseline possible physiological data to the received physiological sensor data with the processor of the robotic athletic training system; and
adjusting the velocity of the robotic athletic training system in response to the physiological data comparison.

19. The method of claim 18, further comprising:
receiving personal information about the individual prior to receiving the received physiological sensor data.

20. The method of claim 19, wherein the personal information comprises one of prior injury information, height, weight, gender, an athletic goal, intended athletic environment, intended athletic duration, and intended workout intensity.

21. The system of claim 18, wherein the physiological sensor data comprises at least one of respiratory data and cardiac data.

22. The method of claim 16, wherein the received surface data is optical data indicating the position of a line on a track in the environment.

* * * * *